United States Patent
Obara et al.

(10) Patent No.: US 11,414,654 B2
(45) Date of Patent: *Aug. 16, 2022

(54) NUCLEOSIDASE AGENT HAVING REDUCED CONTAMINANT ACTIVITY

(71) Applicants: AMANO ENZYME INC., Nagoya (JP); SUNTORY HOLDINGS LIMITED, Osaka (JP)

(72) Inventors: Takakiyo Obara, Kakamigahara (JP); Keita Okuda, Kakamigahara (JP); Tomoko Fujimura, Tokyo (JP); Ikuma Mizuguchi, Fuchu (JP); Tomoyuki Nakahama, Fuchu (JP)

(73) Assignees: AMANO ENZYME INC., Nagoya (JP); SUNTORY HOLDINGS LIMITED, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/966,997

(22) PCT Filed: Jan. 30, 2019

(86) PCT No.: PCT/JP2019/003244
§ 371 (c)(1),
(2) Date: Aug. 3, 2020

(87) PCT Pub. No.: WO2019/155969
PCT Pub. Date: Aug. 15, 2019

(65) Prior Publication Data
US 2021/0024911 A1    Jan. 28, 2021

(30) Foreign Application Priority Data
Feb. 9, 2018 (JP) .............................. JP2018-022542

(51) Int. Cl.
*C12N 9/24* (2006.01)

(52) U.S. Cl.
CPC .................................. *C12N 9/2497* (2013.01)

(58) Field of Classification Search
CPC .................................................. C12N 9/2427
See application file for complete search history.

(56) References Cited

U.S. PATENT DOCUMENTS

| | | |
|---|---|---|
| 6,013,288 A | 1/2000 | Shibano et al. |
| 6,066,484 A | 5/2000 | Hatanaka et al. |
| 2019/0177712 A1 | 6/2019 | Okuda et al. |
| 2019/0223480 A1 | 7/2019 | Okuda |

FOREIGN PATENT DOCUMENTS

| | | |
|---|---|---|
| JP | H10-57063 A | 3/1998 |
| JP | 2004-113189 A | 4/2004 |
| JP | 3824326 B2 | 9/2006 |
| JP | 3824353 B2 | 9/2006 |
| JP | 2012-125205 A | 7/2012 |
| WO | 1996/025483 A1 | 8/1996 |
| WO | 2018/034289 A1 | 2/2018 |
| WO | 18/066617 A1 | 4/2018 |

OTHER PUBLICATIONS

Studer. Residue mutations and their impact on protein structure and function: detecting beneficial and pathogenic changes. Biochem. J. (2013) 449, 581-594.*

Nielsen. A0A1V6RRD9_9EURO. UniProtKB/TrEMBL Database. Jun. 7, 2017.*

International Search Report dated Apr. 16, 2019, issued for PCT/JP2019/003244.

Database Uniprot [Online] De Vries R.P. et al: "IU_nuc_hydro domain-containing protein", Apr. 12, 2017, XP055853535, Database accession No. A0A1Q5SZH4. (cited in the Oct. 21, 2021 Search Report issued for EP1975075.8).

Supplementary European Search Report completed Oct. 21, 2021, issued in the corresponding European application of EP1975075.8.

* cited by examiner

*Primary Examiner* — Yong D Pak
(74) *Attorney, Agent, or Firm* — Locke Lord LLP

(57) ABSTRACT

An object of the present invention is to provide an enzyme preparation useful for reducing purine bodies, especially, in beer or beer-based beverages, and use thereof. Provided is a nucleosidase preparation having an activity ratio (U/U), which is guanine deaminase activity per nucleosidase activity, of 0.4 or less.

10 Claims, 25 Drawing Sheets

Specification includes a Sequence Listing.

|  |  | Peak 1 | Peak 2 | Peak 3 |
|---|---|---|---|---|
| SDS-PAGE molecular weight | Sugar chain present | About 50 kDa | About 50 kDa | About 53 kDa |
|  | Sugar chain absent | About 40 kDa | About 40 kDa | About 48 kDa |
| Gel filtration molecular weight | | About 230 kDa | About 230 kDa | About 126 kDa |
| N-terminal amino acid sequence | | ADKHYAIMDNDWYTA | ADKHYAIMDNDWYTA | VETKLIFLT |
|  |  | SEQ ID NO: 7 | SEQ ID NO: 8 | SEQ ID NO: 9 |

*Fig. 7*

| | |
|---|---|
| Probe sequence | PN1: GAGGATCCCGAAACCTTCCTACGTGTCAAGGAGGTCGTTGTGATGGGTGGAGCAATCAAACCAGCCTGGAAATGTAAACCCGTCGAAACACCCATTTGATAATAAGTCATTAAACCGCGGATTGACTAGGTCACCCCCGTTGACTCAACGCCTACGCAGACGCCGTTGCAGCTGCGGAGTCTTTGGCGTCGACATCGAGTCTGCGTCTCTTCCGCGCTGAAACTGAGTCCAAACGGAGTCCAACTACTTGGCTGTACCCTGCAAAGCTCAGCCGACAATTGACTCTGCGTCTCCGGACATCACCCTGCGCGCCATAAGCTGTCCGCGCCAATTCCGCCAAGCAGTTGAGCCTCTCCTCGCAACAGGGCTCACCCTCGCGTCGAATGGGTGACAGCATTCATGGACACCCTGTCTGTGGTATGCCCTTACAGACAGAGGATTGGCACCACCCCGGCCATGAGGGCGATGAAGCCCAGCCCAGTCTCCACGACCTGAGTCTCGTGTTGAGAGACATTCGTGTTGAGAGACATTGGGCC SEQ ID NO: 18 |
| Probe sequence | PN2: AGACACCGCAAACACCTGGCAGCCTCAGGTCGGCTCTGCACGGTCGCTGGAAGCTGTGGAACTCTGAGCTGTATCCCCGTTTACCCAGGCTCGACATGGCCCGGTCATCAACACCCCGACCGGTTCCAGGCGTGGGAAATGGTTCATGGCAAGCTGCCATGGGAGGGTGCTTTTGGGCCGGAGAACAAAGACTCTCGAGGGCGAAACATCGTCGAGATCCTGCCAACCGTATCGTGCACAAGTACCCGGCCAGGTGGAAGGGTTCCCAAGGCAAGGGCAAGAACATCTGCTGGCCTCATGGTGCGCTGTGCCCCAACTTCATGGCGATGAGATCCCCAGTTGCATCGATCTCCTGGCTAAGGAGTTGGTCTGGATCTACTCGTCGATTTGAATATGCTCCAGGCCACTGGAAGTGTCTTGCTGGCTGATCTTCAATCTG SEQ ID NO: 19 |

Fig. 8

| | PN1 |
|---|---|
| Genomic sequence (SEQ ID NO: 4) | ATGGCACCTAAGAAAATCATCATTGACACTGACCCGGTAAGTTGCCTATACATAACTGAAGATATCTACTCCTAGACATG<br>CTAATGAATGATTAGGGTATCGATGACATCCTGGCACTGCTGCTGGCTCTGTCATCTAAGCCAGAGGATGTTGAGATTCT<br>ACTTATCTCTTTAACATTTGGAAACATTGAGGTGAAGAAGTGAGTGCTACCTTTGTGAAAGTCAACTCAGAAACGAGTTC<br>AGCCTATTTATTTCCTTACAGCTGTCTTCGAAATGTGGTCTCCATGTTTCATATCCTCGAGCGCGAGATCCAGTGGCGTC<br>GTGGTAACGGGAAGTCCGAAGGCTATGGCACTATGCGTGCTTTCCGCCCAGTAGTAGCCGTGGGAGCGGAAGATCCCTTG<br>GAAGACCAGAAGATGCTCGCTGATTATTTCCGTAAGTGCTTTGTGGTTTTGAAAGTCAATCACGTCGCTGAGAATTACCC<br>CGCAGATGGAACCGATGGCGTTGGTGGCATCCATGCTAGTGTAGGCTAAACGCCCACCTTATTCGACCAATGATGTACCG<br>ATTTTCTAACACTATCTGGACAGCACCCACATCTCACTCCAAGCAAGGCTGGGAGCATCTATTCACCCCGGCCGTGGAT<br>CGCCAGGGGATCGAGCCTGTGCAAACGGGAGCTGGTCCCGGCCGACCATTCCTTTATCCCATCAAGACTACCTGCAGACAA<br>GGAGATTCTTCGTGCACTGCGCCAGAATGAGCCTGACACCGTGACTCTCGTGGCCGGTTGGTCCACTGACCAACTTGGCCT<br>TGGCAGGAGCAGAGGATCCCGAAACCTTCCTACGTGTCAAGGAGGTCGTTGTGATGGGTGGAGCAATCAACCAGCCTGGA<br>AATGTATGAACCCCGTCGAAACACCCATTTGATAATAAGTCATTAACCGCGATTGACTAGGTCACCCCCGTTGGAGAATT<br>CAACGCGTACGCAGACGCCGTTGCAGCTGCGGAGTCTTTGCGCTGACATCACCTAATCCCAACTCGACTCTACCGACCGA<br>CCACGAGTCCACTACTTGGCCTGTACCCTGCAAAGCTCAGCCGACAATTGACTCTGCGTCTCTTCCCGCTGGACATCACC<br>CTGCGGCATAACCTGTCCGCGGCCAATTCCGCCAAGCAGTTGAGCCTCTCCTCGGCAACAGGCTCACCCCTCGCTGAATG<br>GGTGACAGCATTCATGGGACACACGTTCCGAACCCTGGAACGCCTGCACCCCGGCCATGAGGGCGATGAAGCCCAGCTGA<br>GTCTCACGACCGTGTCTGTGTGTGGTATGCCCTTACAGCAGAGGATTGGCACTGGACTCCCTCCGCCAATTCCCCAGAG<br>GACATTCGTGTTGAGACATTGGGCCAGTGGACGCGTGGTATGTGCGTAATCGATGGCGAAACCGCCATAAGATTGATGG<br>CGACGAGGAAAGCTCGAGTGATCATGGTCTGTGGTTGAGTGCTCGTGCAGGAAACCGCATTTTGCCGAATGGATGGATCGC<br>CAGCCGAACACACGTTCGGCAAGATCCTCATCGATAGAATCTTCCACTAA |
| | PN2 |
| Genomic sequence (SEQ ID NO: 6) | ATGCATTTCCCTGTTTCATTGCCGCTGTTGTGCGGCTCTTTGCTGCCTCTCATCACCGGCACCCTGGCAGTGCCCAAGGC<br>CTCGCGTGCCGACAAGCACTATGCCATCATGGACAATGATTGGTACACAGCGGGTTTCGTGCCTTACCTGATCGCCCTCG<br>ATGGGGATGTGGAGGTTCTGGGCCTAGCCTCTGGTTAGTGTTGATCCGCATCCATACCGGTTTTCCTTCAAGGTCTGCAG<br>TGCTAAGCTTCCATGTCATATCAGACACCGCAAAGACCTGGCAGCCTCAGGTCGGTCTGCACGCTGTCGCAACTCTGGAAC<br>CTGGCAACTTGAGCTGTATCGCCGTTTACCCAGGCTCGACATGCCGGCTCATCAACACGCCCAACGCGTTCCAGGCGTGG<br>GAAATGGTTCATGGCAAGCTGCCATGGGAGGGTGCTTTTGCGCCGGAGAACAAGACTCTCGAGGCCGAGGGTAACGATCC<br>TAGCTCTGGCAACCCGAAACGGTATCGTCAAGGCCGCTTTCAAGGAAGGGTTCCCCAAGGGCAAGCCCGAGAACAGAACAT<br>CTGCTGCCAAACTTCATGGTCGAGATGGTGCACAAGTACCCGGCCAGGTCTCGATCTACTCTGCTGGAGCCCTGACCAAT<br>GTTGCGCTGGCTGTGCCCATGGATCCCCAGTTTGCATCTCTGGCTAAGGAGTTGGTTATCATGCGTGGATACGTCGATTT<br>GAATATGCTCCAGGCCACTGGAAGTGTCTTGCTGCCTGATCTTCAATCTGATGTATGTTTCATTCCCGCTTCTATCACG<br>TGTGTTGATCTGCTAACTTGTCTTTAGATCAACTTGATCATTGATCCCGAGGCCTCCAAGATCGCATTGACTGCCGAATT<br>CCCCAATATCACCATCGCCGGTAACGTCGCCAACCAGGTCTTTCCTACCAAGGAGTTCGTCGACCGAGATCGCCTCCGTTC<br>CAAACGCCTAGAGCAAGCTGTTCCACGACTACTACGATCTGTCCTTCCCCTTCTGGGATGAGACGGCTGCCGCTGATG<br>GTTGACCCTACTCTTGCTACCAACCAGACCTCTGCTGAGTTTAATCTCGCATTGACACTTGTATGAACAAATCTAACAGC<br>TTATAGTCTTCCTGCAGTGGATACCGCTTATGGTAGGCCCAACTATGGTAACATTCACGTTTACCAGAACGCTCTTCCG<br>CCTGTTGGTATCCGGGAGGTCAACTTTGTCTTCCAGGTTGATGGGGATAGACTTAAGCAGCGCATCAAGCACTCTCTGCA<br>GTACCCCAAGTCATGCGCGGACCTGAGAAATGAGCGTTGA |

*Fig. 9*

| | PN1 |
|---|---|
| cDNA sequence (SEQ ID NO: 3) | ATGGCAGGTAAGAAAATCATCATTGACACTGACCCGGGTATCGATGACATCCTGGCACTGCTGCTGGCTCTGTCATCTAAGCCAGAGGATGTTGAGATTCTACTTATCTCTTTAACATTTGGAAACATTGAGGTGAAGAACTGTCTTCGAAATGTGGTCTCCATGTTTCATATCCTCGAGCGCGAGATCCAGTGGCGTCGTGGTAACGGCAAGTCCGAAGGCTATGGCACTATGCGTGCTTTCCGCCCAGTAGTAGCCGTGGGAGCGGAAGATCCCTTGGAAGACCAGAAGATGCTCGCTGATTATTTCCATGGAACCGATGGCCTTGGTGGCATCCATGCTAGTCACCCACATCTCACTCCAAGCAAGGCCTGGGAGCATCTATTCACCCCGGCCGTGGATCCCCAGGGGATCGAGGCTGTGCAAACGGGAGCTGGTCCGGCGACCATTCCTTTATCCCATCAAGACTACCTGCACAGAAGGAGATTCTTCGTGCACTGCGCCAGAATGAGCCTGACACCGTGACTCTCGTGGCGGTTGTCCACTGACCAACTTGGCCTTGGCAGCAGGAGGATCCCGAAACCTTCCTACGTGTCAAGGAGGTCGTTGTGATGGGTGGAGCAATCAACCAGCCTGGAAATGTCAGCCCCGTTGGAGAATTCAAGGCCTACGCAGACGCCGTTGCAGCTGCGCGAGTCTTTGCGGTGACATCACCTAATCCCAACTCGACTCTACCACCGACCACGAGTCCACTAGTTGGCCTGTACCCTGCAAAGCTCAGCCGACAATTGACTCTGCGTCTCTTCCCGGCTGGACATGACCCTGCGCCATAACCTGTCCGGCGGCCAATTCCGCCAAGCAGTTGAGCCTCTCCTCGCAACAGGCTCACCCCTCGCTGAATGGGTGACAGCATTCATGGACACACGTTCCGAACCCTGGAACGCCTGCACCCGGCCATGAGGGCGATGAAGCCCAGCTGAGTCTCCACGACCCTGTCTGTGTGTGGTATGCCCTTACAGCAGAGGATTCGCACTGGACTCCCTCCGCCAATTCCCCAGAGGACATTCGTGTTGAGACATTGGGCCAGTGGACGCGTGGTATGTGCGTAATCGATGGCCGAAACCGCCATAAGATTGATGGCGACGAGGAAAGCTCGAGTCATCATGGTCTGTGGTTGAGTGCTCGTGCAGGAAACCGCATTTTGCCGAATGGATGGATCGCCAGCCGAACACACGTTCGGCAAGATCCTCATCGATAGAATCTTCCACTAA |
| | PN2 |
| cDNA sequence (SEQ ID NO: 5) | ATGCATTTCCCTGTTTCATTGCCGCTGTTGTGCCGCTCTTTGCTGCCTCTCATCACCGGCACCCTGGGAGTGCCCAAGGCCTCGCGTGCCGACAAGCACTATGCCATCATGGACAATGATTGGTACACAGCGGGTTTCGTGCCTTACGTGATCGCCCATATGGCGATGTGGAGGTTCTGGGCCTAGCCTCTGACACCGCAAACACCTGGCAGCCTCAGGTCGCTCTGCACGCTGTCGCAACTCTGGAAGCTGGCAACTTGAGCTGTATCCCCCTTTACCCAGGCTCGACATGGCCGCTCATCAACACCCCCAACCGCTTCCAGGCGTGGGAAATGGTTCATGGCAAGCTGCCATGGGAGGGTGCTTTTGCGCCGGAGAACAAGACTCTCGAGGCCGAGGGTAACGATCCTACCTCTGGCAACCCCAACCGTATCGTCAAGGCGGCTTTCAAGGAAGCGTTCCCCAAGGGCAACCCCGAGAACAGAACATCTGCTGCCAACTTCATGGTCGAGATGGTGCACAAGTACCGGGCCAGGTCTCGATCTACTCTGCTGGAGCCCTGACCAATGTTGCGCTGGCTGTGCCGCATGGATCCCCAGTTTGCATCTCTGGCTAAGGAGTTGGTTATCATGGGTGGATACGTCGATTTGAAATATGGTCCAGGCCACTGGAACTGTCTTGCTGGCTGATCTTCAATCTGATATCAACTTGATGATTGATCCCGAGGCCTCCAAGATCGCATTGACTGCCGAATTCCCAATATCACCATCGCCGGTAACGTCGCCAACCAGGTCTTTCCTACCAAGGAGTTCGTCGACGAGATCGCCTCCGTTCCAAACCCCTACAGCAAGCTCTTCCACGACTACTACGATCTGTCCTTCCCCTTCTGGGATGAGACGGCTGCCGCGCTGATGGTTGACCCTACTCTTGCTACCAACCAGACCTCTGTCTTCCTCGACGTGGATACCGCTTATGGTAGCCCAACTATGGTAACATTCACGTTACCAGAAGGCTCTTGCCCCTGTTGGTATCCGGGAGGTCAACTTTGTCTTCCAGGTTGATGGGGATAGACTTAAGGAGCCGATCAAGCACTCTCTGCAGTACCCCAAGTCATGCCCGACCTGAGAAATGAGCGTTGA |

*Fig. 10*

PN1 (peak 3) (SEQ ID NO: 1)

MAPKKIIIDTDPGIDDILALLLALSSKPEDVEILLISLTFGNIEVKNCLRNVVSMFHILE
REIQWRRGNGKSEGYGTMRAFRPVVAVGAEDPLEDQKMLADYFHGTDGLGGIHASHPHLT
PSKAWEHLFTPAVDPQGIEPVQTGAGPGDHSFIPSRLPAHKEILRALRQNEPDTVTLVAV
GPLTNLALAAAEDPETFLRVKEVVVMGGAINQPGNVTPVGEFNAYADAVAAARVFALTSP
NPNSTLPPTTSPLLGLYPAKLSRQLTLRLFPLDITLRHNLSRGQFRQAVEPLLATGSPLA
EWVTAFMGHTFRTLERLHPGHEGDEAQLSLHDPVCVWYALTAEDSHWTPSANSPEDIRVE
TLGQWTRGMCVIDGRNRHKIDGDEESSSDHGLWLSARAGNRILRMDGSPAEHTFGKILID
RIFH*

PN2 (peaks 1 and 2) (SEQ ID NO: 2)

MHFPVSLPLLCGSLLPLITGTLAVPKASRADKHYAIMDNDWYTAGFVPYLIALDGDVEVL
GLASDTANTWQPQVALHAVATLEAGNLSCIPVYPGSTWPLINTPNRFQAWEMVHGKLPWE
GAFAPENKTLEAEGNDPTSGNPNRIVKAAFKEGFPKGKPENRTSAANFMVEMVHKYPGQV
SIYSAGALTNVALAVRMDPQFASLAKELVIMGGYVDLNMLQATGSVLLADLQSDINLMID
PEASKIALTAEFPNITIAGNVANQVFPTKEFVDEIASVPNPYSKLFHDYYDLSFPFWDET
AAALMVDPTLATNQTSVFLDVDTAYGSPNYGNIHVYQKALAPVGIREVNFVFQVDGDRLK
QRIKHSLQYPKSCADLRNER*

*Fig. 11*

|  | PN1 | PN2 |
|---|---|---|
| Number of bases (cDNA) | 1,275 bp | 1,143 bp |
| Number of introns | 5 | 3 |
| Amino acid length | 424 aa | 380 aa |
| Estimated molecular weight | 46,400 | 41,600 |
| Estimated pI | 5.7 | 5.0 |

*Fig. 12*

```
SEQUENCE LISTING

<160> NUMBER OF SEQ ID NOS: 24

<210> SEQ ID NO 1
<211> LENGTH: 424
<212> TYPE: PRT
<213> ORGANISM: Penicillium multicolor

<400> SEQUENCE: 1

Met Ala Pro Lys Lys Ile Ile Ile Asp Thr Asp Pro Gly Ile Asp Asp
1               5                   10                  15
```

```
Ile Leu Ala Leu Leu Ala Leu Ser Ser Lys Pro Glu Asp Val Glu
             20                  25                  30

Ile Leu Leu Ile Ser Leu Thr Phe Gly Asn Ile Glu Val Lys Asn Cys
         35                  40                  45

Leu Arg Asn Val Val Ser Met Phe His Ile Leu Glu Arg Glu Ile Gln
 50                  55                  60

Trp Arg Arg Gly Asn Gly Lys Ser Glu Gly Tyr Gly Thr Met Arg Ala
 65                  70                  75                  80

Phe Arg Pro Val Val Ala Val Gly Ala Glu Asp Pro Leu Glu Asp Gln
                 85                  90                  95

Lys Met Leu Ala Asp Tyr Phe His Gly Thr Asp Gly Leu Gly Gly Ile
             100                 105                 110

His Ala Ser His Pro His Leu Thr Pro Ser Lys Ala Trp Glu His Leu
         115                 120                 125

Phe Thr Pro Ala Val Asp Pro Gln Gly Ile Glu Pro Val Gln Thr Gly
130                 135                 140

Ala Gly Pro Gly Asp His Ser Phe Ile Pro Ser Arg Leu Pro Ala His
145                 150                 155                 160

Lys Glu Ile Leu Arg Ala Leu Arg Gln Asn Glu Pro Asp Thr Val Thr
                165                 170                 175

Leu Val Ala Val Gly Pro Leu Thr Asn Leu Ala Leu Ala Ala Ala Glu
            180                 185                 190

Asp Pro Glu Thr Phe Leu Arg Val Lys Glu Val Val Met Gly Gly
        195                 200                 205

Ala Ile Asn Gln Pro Gly Asn Val Thr Pro Val Gly Glu Phe Asn Ala
210                 215                 220

Tyr Ala Asp Ala Val Ala Ala Arg Val Phe Ala Leu Thr Ser Pro
225                 230                 235                 240

Asn Pro Asn Ser Thr Leu Pro Pro Thr Thr Ser Pro Leu Leu Gly Leu
                245                 250                 255

Tyr Pro Ala Lys Leu Ser Arg Gln Leu Thr Leu Arg Leu Phe Pro Leu
            260                 265                 270

Asp Ile Thr Leu Arg His Asn Leu Ser Arg Gly Gln Phe Arg Gln Ala
        275                 280                 285

Val Glu Pro Leu Leu Ala Thr Gly Ser Pro Leu Ala Glu Trp Val Thr
290                 295                 300

Ala Phe Met Gly His Thr Phe Arg Thr Leu Glu Arg Leu His Pro Gly
305                 310                 315                 320

His Glu Gly Asp Glu Ala Gln Leu Ser Leu His Asp Pro Val Cys Val
                325                 330                 335

Trp Tyr Ala Leu Thr Ala Glu Asp Ser His Trp Thr Pro Ser Ala Asn
            340                 345                 350

Ser Pro Glu Asp Ile Arg Val Glu Thr Leu Gly Gln Trp Thr Arg Gly
        355                 360                 365

Met Cys Val Ile Asp Gly Arg Asn Arg His Lys Ile Pro Gly Asp Glu
370                 375                 380

Glu Ser Ser Ser Asp His Gly Leu Trp Leu Ser Ala Arg Ala Gly Asn
385                 390                 395                 400

Arg Ile Leu Arg Met Asp Gly Ser Pro Ala Glu His Thr Phe Gly Lys
                405                 410                 415

Ile Leu Ile Asp Arg Ile Phe His
            420
```

```
<210> SEQ ID NO 2
<211> LENGTH: 380
<212> TYPE: PRT
<213> ORGANISM: Penicillium multicolor

<400> SEQUENCE: 2

Met His Phe Pro Val Ser Leu Pro Leu Cys Gly Ser Leu Leu Pro
1               5                   10                  15

Leu Ile Thr Gly Thr Leu Ala Val Pro Lys Ala Ser Arg Ala Asp Lys
            20                  25                  30

His Tyr Ala Ile Met Asp Asn Asp Trp Tyr Thr Ala Gly Phe Val Pro
        35                  40                  45

Tyr Leu Ile Ala Leu Asp Gly Asp Val Glu Val Leu Gly Leu Ala Ser
    50                  55                  60

Asp Thr Ala Asn Thr Trp Gln Pro Gln Val Ala Leu His Ala Val Ala
65                  70                  75                  80

Thr Leu Glu Ala Gly Asn Leu Ser Cys Ile Pro Val Tyr Pro Gly Ser
                85                  90                  95

Thr Trp Pro Leu Ile Asn Thr Pro Asn Arg Phe Gln Ala Trp Glu Met
            100                 105                 110

Val His Gly Lys Leu Pro Trp Glu Gly Ala Phe Ala Pro Glu Asn Lys
        115                 120                 125

Thr Leu Glu Ala Glu Gly Asn Asp Pro Thr Ser Gly Asn Pro Asn Arg
    130                 135                 140

Ile Val Lys Ala Ala Phe Lys Glu Gly Phe Pro Lys Gly Lys Pro Glu
145                 150                 155                 160

Asn Arg Thr Ser Ala Ala Asn Phe Met Val Glu Met Val His Lys Tyr
                165                 170                 175

Pro Gly Gln Val Ser Ile Tyr Ser Ala Gly Ala Leu Thr Asn Val Ala
            180                 185                 190

Leu Ala Val Arg Met Asp Pro Gln Phe Ala Ser Leu Ala Lys Glu Leu
        195                 200                 205

Val Ile Met Gly Gly Tyr Val Asp Leu Asn Met Leu Gln Ala Thr Gly
    210                 215                 220

Ser Val Leu Leu Ala Asp Leu Gln Ser Asp Ile Asn Leu Met Ile Asp
225                 230                 235                 240

Pro Glu Ala Ser Lys Ile Ala Leu Thr Ala Glu Phe Pro Asn Ile Thr
                245                 250                 255

Ile Ala Gly Asn Val Ala Asn Gln Val Phe Pro Thr Lys Glu Phe Val
            260                 265                 270

Asp Glu Ile Ala Ser Val Pro Asn Pro Tyr Ser Lys Leu Phe His Asp
        275                 280                 285

Tyr Tyr Asp Leu Ser Phe Pro Phe Trp Asp Thr Ala Ala Ala Leu
    290                 295                 300

Met Val Asp Pro Thr Leu Ala Thr Asn Gln Thr Ser Val Phe Leu Asp
305                 310                 315                 320

Val Asp Thr Ala Tyr Gly Ser Pro Asn Tyr Gly Asn Ile His Val Tyr
                325                 330                 335

Gln Lys Ala Leu Ala Pro Val Gly Ile Arg Glu Val Asn Phe Val Phe
            340                 345                 350

Gln Val Asp Gly Asp Arg Leu Lys Gln Arg Ile Lys His Ser Leu Gln
        355                 360                 365

Tyr Pro Lys Ser Cys Ala Asp Leu Arg Asn Glu Arg
    370                 375                 380
```

<210> SEQ ID NO 3
<211> LENGTH: 1275
<212> TYPE: DNA
<213> ORGANISM: Penicillium multicolor

<400> SEQUENCE: 3

| | | | | | |
|---|---|---|---|---|---|
| atggcaccta | agaaaatcat | cattgacact | gacccgggta | tcgatgacat | cctggcactg | 60 |
| ctgctggctc | tgtcatctaa | gccagaggat | gttgagattc | tacttatctc | tttaacattt | 120 |
| ggaaacattg | aggtgaagaa | ctgtcttcga | aatgtggtct | ccatgtttca | tatcctcgag | 180 |
| cgcgagatcc | agtggcgtcg | tggtaacggc | aagtccgaag | gctatggcac | tatgcgtgct | 240 |
| ttccgcccag | tagtagccgt | gggagcggaa | gatcccttgg | aagaccagaa | gatgctcgct | 300 |
| gattatttcc | atggaaccga | tggccttggt | ggcatccatg | ctagtcaccc | acatctcact | 360 |
| ccaagcaagg | cctgggagca | tctattcacc | ccggccgtgg | atcccaggg | gatcgagcct | 420 |
| gtgcaaacgg | gagctggtcc | cggcgaccat | tcctttatcc | catcaagact | acctgcacac | 480 |
| aaggagattc | ttcgtgcact | cgccagaat | gagcctgaca | ccgtgactct | cgtggcggtt | 540 |
| ggtccactga | ccaacttggc | cttggcagca | gcagaggatc | ccgaaacctt | cctacgtgtc | 600 |
| aaggaggtcg | ttgtgatggg | tggagcaatc | aaccagcctg | gaaatgtcac | ccccgttgga | 660 |
| gaattcaacg | cctacgcaga | cgccgttgca | gctgcgcgag | tctttgcgct | gacatcacct | 720 |
| aatcccaact | cgactctacc | accgaccacg | agtccactac | ttggcctgta | ccctgcaaag | 780 |
| ctcagccgac | aattgactct | gcgtctcttc | ccgctggaca | tcaccctgcg | ccataacctg | 840 |
| tcccgcggcc | aattccgcca | agcagttgag | cctctcctcg | caacaggctc | accctcgct | 900 |
| gaatgggtga | cagcattcat | gggacacacg | ttccgaaccc | tggaacgcct | gcaccccggc | 960 |
| catgagggcg | atgaagccca | gctgagtctc | cacgaccctg | tctgtgtgtg | gtatgccctt | 1020 |
| acagcagagg | attcgcactg | gactccctcc | gccaattccc | cagaggacat | tcgtgttgag | 1080 |
| acattgggcc | agtggacgcg | tggtatgtgc | gtaatcgatg | gccgaaaccg | ccataagatt | 1140 |
| gatggcgacg | aggaaagctc | gagtgatcat | ggtctgtggt | tgagtgctcg | tgcaggaaac | 1200 |
| cgcattttgc | gaatggatgg | atcgccagcc | gaacacacgt | tcggcaagat | cctcatcgat | 1260 |
| agaatcttcc | actaa | | | | | 1275 |

<210> SEQ ID NO 4
<211> LENGTH: 1016
<212> TYPE: DNA
<213> ORGANISM: Penicillium multicolor

<400> SEQUENCE: 4

| | | | | | |
|---|---|---|---|---|---|
| gtacccattt | tctaacacta | tctggacagc | acccacatct | cactccaagc | aaggcctggg | 60 |
| agcatctatt | caccccggcc | gtggatcccc | aggggatcga | gcctgtgcaa | acgggagctg | 120 |
| gtcccggcga | ccattccttt | atcccatcaa | gactacctgc | acacaaggag | attcttcgtg | 180 |
| cactgcgcca | gaatgagcct | gacaccgtga | ctctcgtggc | ggttggtcca | ctgaccaact | 240 |
| tggccttggc | agcagcagag | gatcccgaaa | ccttcctacg | tgtcaaggag | gtcgttgtga | 300 |
| tgggtggagc | aatcaaccag | cctggaaatg | tatgaacccc | gtcgaaacac | ccatttgata | 360 |
| ataagtcatt | aaccgcgatt | gactaggtca | ccccgttgg | agaattcaac | gcctacgcag | 420 |
| acgccgttgc | agctgcgcga | gtctttgcgc | tgacatcacc | taatcccaac | tcgactctac | 480 |
| caccgaccac | gagtccacta | cttggcctgt | accctgcaaa | gctcagccga | caattgactc | 540 |
| tgcgtctctt | cccgctggac | atcaccctgc | gccataacct | gtcccgcggc | caattccgcc | 600 |

```
aagcagttga gcctctcctc gcaacaggct caccccctcgc tgaatgggtg acagcattca      660
tgggacacac gttccgaacc ctggaacgcc tgcaccccgg ccatgagggc gatgaagccc      720
agctgagtct ccacgaccct gtctgtgtgt ggtatgccct tacagcagag gattcgcact      780
ggactccctc cgccaattcc ccagaggaca ttcgtgttga cattgggc cagtggacgc        840 gtggtatgtg cgtaatcgat ggccgaaacc gccataagat tgatggcgac gaggaaagct     900
cgagtgatca tggtctgtgg ttgagtgctc gtgcaggaaa ccgcattttg cgaatggatg     960
gatcgccagc cgaacacacg ttcggcaaga tcctcatcga tagaatcttc cactaa        1016
```

<210> SEQ ID NO 5
<211> LENGTH: 1143
<212> TYPE: DNA
<213> ORGANISM: Penicillium multicolor

<400> SEQUENCE: 5

```
atgcatttcc ctgtttcatt gccgctgttg tgcggctctt tgctgcctct catcaccggc        60
accctggcag tgcccaaggc ctcgcgtgcc gacaagcact atgccatcat ggacaatgat      120
tggtacacag cgggtttcgt gccttacctg atcgccctcg atggcgatgt ggaggttctg      180
ggcctagcct ctgacaccgc aaacacctgg cagcctcagg tcgctctgca cgctgtcgca      240
actctggaag ctggcaactt gagctgtatc cccgtttacc caggctcgac atggccgctc      300
atcaacaccc ccaaccgctt ccaggcgtgg gaaatggttc atggcaagct gccatgggag      360
ggtgcttttg cgccggagaa caagactctc gaggccgagg gtaacgatcc tacctctggc      420
aaccccaacc gtatcgtcaa ggccgctttc aaggaagggt tccccaaggg caagcccgag      480
aacagaacat ctgctgccaa cttcatggtc gagatggtgc acaagtaccc cggccaggtc      540
tcgatctact ctgctggagc cctgaccaat gttgcgctgg ctgtgcgcat ggatcccag      600 tttgcatctc tggctaagga gttggttatc atgggtggat acgtcgattt gaatatgctc      660
caggccactg gaagtgtctt gctggctgat cttcaatctg atatcaactt gatgattgat      720
cccgaggcct ccaagatcgc attgactgcc gaattcccca atatcaccat cgccggtaac     780
gtcgccaacc aggtctttcc taccaaggag ttcgtcgacg agatcgcctc cgttccaaac     840
ccctacagca agctcttcca cgactactac gatctgtcct tccccttctg ggatgagacg     900
gctgccgcgc tgatggttga ccctactctt gctaccaacc agacctctgt cttcctcgac    960
gtggataccg cttatggtag ccccaactat ggtaacattc acgtttacca gaaggctctt    1020
gcccctgttg gtatccggga ggtcaacttt gtcttccagg ttgatgggga tagacttaag   1080
cagcgcatca agcactctct gcagtacccc aagtcatgcg ccgacctgag aaatgagcgt   1140
tga                                                                  1143
```

<210> SEQ ID NO 6
<211> LENGTH: 847
<212> TYPE: DNA
<213> ORGANISM: Penicillium multicolor

<400> SEQUENCE: 6

```
acgatcctac ctctggcaac cccaaccgta tcgtcaaggc cgctttcaag gaagggttcc       60
ccaagggcaa gcccgagaac agaacatctg ctgccaactt catggtcgag atggtgcaca     120
agtaccccgg ccaggtctcg atctactctg ctggagccct gaccaatgtt gcgctggctg    180
tgcgcatgga tccccagttt gcatctctgg ctaaggagtt ggttatcatg ggtggatacg    240
```

```
tcgatttgaa tatgctccag gccactggaa gtgtcttgct ggctgatctt caatctgatg    300
tatgtttcat tcccggcttc tatcagctgt gttcatctgc taacttctct ttagatcaac    360
ttgatgattg atcccgaggc ctccaagatc gcattgactg ccgaattccc caatatcacc    420
atcgccggta acgtcgccaa ccaggtcttt cctaccaagg agttcgtcga cgagatcgcc    480
tccgttccaa accccctacag caagctcttc cacgactact acgatctgtc cttccccttc    540
tgggatgaga cggctgccgc gctgatggtt gaccctactc ttgctaccaa ccagacctct    600
ggtgagttta atctcgcatt gacacttgta tgaacaaatc taacagctta tagtcttcct    660
cgacgtggat accgcttatg gtagccccaa ctatggtaac attcacgttt accagaacgc    720
tcttgcccct gttggtatcc gggaggtcaa ctttgtcttc caggttgatg gggatagact    780
taagcagcgc atcaagcact ctctgcagta ccccaagtca tgcgccgacc tgagaaatga    840
gcgttga                                                              847
```

<210> SEQ ID NO 7
<211> LENGTH: 15
<212> TYPE: PRT
<213> ORGANISM: Penicillium multicolor

<400> SEQUENCE: 7

Ala Asp Lys His Tyr Ala Ile Met Asp Asn Asp Trp Tyr Thr Ala
1               5                   10                  15

<210> SEQ ID NO 8
<211> LENGTH: 15
<212> TYPE: PRT
<213> ORGANISM: Penicillium multicolor

<400> SEQUENCE: 8

Ala Asp Lys His Tyr Ala Ile Met Asp Asn Asp Trp Tyr Thr Ala
1               5                   10                  15

<210> SEQ ID NO 9
<211> LENGTH: 9
<212> TYPE: PRT
<213> ORGANISM: Penicillium multicolor

<400> SEQUENCE: 9

Val Glu Thr Lys Leu Ile Phe Leu Thr
1               5

<210> SEQ ID NO 10
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: inosine
<220> FEATURE:
<221> NAME/KEY: misc_feature
<222> LOCATION: (6)..(6)
<223> OTHER INFORMATION: g or a
<220> FEATURE:
<221> NAME/KEY: misc_feature
<222> LOCATION: (9)..(9)
<223> OTHER INFORMATION: t or c
<220> FEATURE:
<221> NAME/KEY: misc_feature
<222> LOCATION: (10)..(10)
<223> OTHER INFORMATION: a or c
<220> FEATURE:

```
<221> NAME/KEY: misc_feature
<222> LOCATION: (12)..(12)
<223> OTHER INFORMATION: any of a, g, c, or t
<220> FEATURE:
<221> NAME/KEY: misc_feature
<222> LOCATION: (15)..(15)
<223> OTHER INFORMATION: t or c
<220> FEATURE:
<221> NAME/KEY: misc_feature
<222> LOCATION: (16)..(16)
<223> OTHER INFORMATION: t or c
<220> FEATURE:
<221> NAME/KEY: misc_feature
<222> LOCATION: (18)..(18)
<223> OTHER INFORMATION: inosine

<400> SEQUENCE: 10
acnaartaym gnttyytnac                                          20

<210> SEQ ID NO 11
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (4)..(4)
<223> OTHER INFORMATION: any of a, g, c, or t
<220> FEATURE:
<221> NAME/KEY: misc_feature
<222> LOCATION: (7)..(7)
<223> OTHER INFORMATION: any of a, g, c, or t
<220> FEATURE:
<221> NAME/KEY: misc_feature
<222> LOCATION: (9)..(9)
<223> OTHER INFORMATION: g or t
<220> FEATURE:
<221> NAME/KEY: misc_feature
<222> LOCATION: (10)..(10)
<223> OTHER INFORMATION: any of a, g, c, or t
<220> FEATURE:
<221> NAME/KEY: misc_feature
<222> LOCATION: (16)..(16)
<223> OTHER INFORMATION: t or c
<220> FEATURE:
<221> NAME/KEY: misc_feature
<222> LOCATION: (19)..(19)
<223> OTHER INFORMATION: any of a, g, c, or t

<400> SEQUENCE: 11
catnccnckn gtccaytgnc c                                        21

<210> SEQ ID NO 12
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: any of a, g, c, or t
<220> FEATURE:
<221> NAME/KEY: misc_feature
<222> LOCATION: (6)..(6)
<223> OTHER INFORMATION: a, c, or t
<220> FEATURE:
<221> NAME/KEY: misc_feature
<222> LOCATION: (12)..(12)
<223> OTHER INFORMATION: t or c
<220> FEATURE:
<221> NAME/KEY: misc_feature
<222> LOCATION: (15)..(15)
<223> OTHER INFORMATION: t or c
```

```
<220> FEATURE:
<221> NAME/KEY: misc_feature
<222> LOCATION: (18)..(18)
<223> OTHER INFORMATION: t or c
<220> FEATURE:
<221> NAME/KEY: misc_feature
<222> LOCATION: (24)..(24)
<223> OTHER INFORMATION: t or c

<400> SEQUENCE: 12
gcnathatgg ayaaygaytg gtayac                                         26

<210> SEQ ID NO 13
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: any of a, g, c, or t
<220> FEATURE:
<221> NAME/KEY: misc_feature
<222> LOCATION: (6)..(6)
<223> OTHER INFORMATION: any of a, g, c, or t
<220> FEATURE:
<221> NAME/KEY: misc_feature
<222> LOCATION: (9)..(9)
<223> OTHER INFORMATION: t or c
<220> FEATURE:
<221> NAME/KEY: misc_feature
<222> LOCATION: (12)..(12)
<223> OTHER INFORMATION: g or a
<220> FEATURE:
<221> NAME/KEY: misc_feature
<222> LOCATION: (18)..(18)
<223> OTHER INFORMATION: g or a
<220> FEATURE:
<221> NAME/KEY: misc_feature
<222> LOCATION: (21)..(21)
<223> OTHER INFORMATION: any of a, g, c, or t

<400> SEQUENCE: 13
gcngcngtyt crtcccaraa ngg                                            23

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
atggcaccta agaaaatcat cattg                                          25

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
ttagtggaag attctatcga tgagg                                          25

<210> SEQ ID NO 16
<211> LENGTH: 25
<212> TYPE: DNA
<213> ORGANISM: Artificial Sequence
<220> FEATURE:
```

<223> OTHER INFORMATION: primer

<400> SEQUENCE: 16
atgcatttcc ctgtttcatt gccgc                                          25

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
tcaacgctca tttctcaggt cgg                                            23

<210> SEQ ID NO 18
<211> LENGTH: 574
<212> TYPE: DNA
<213> ORGANISM: Artificial Sequence
<220> FEATURE:
<223> OTHER INFORMATION: probe

<400> SEQUENCE: 18
gaggatcccg aaaccttcct acgtgtcaag gaggtcgttg tgatgggtgg agcaatcaac     60
cagcctggaa atgtatgaac cccgtcgaaa cacccatttg ataataagtc attaaccgcg    120
attgactagg tcaccccgt tggagaattc aacgcctacg cagacgccgt tgcagctgcg     180
cgagtctttg cgctgacatc acctaatccc aactcgactc taccaccgac cacgagtcca    240
ctacttggcc tgtaccctgc aaagctcagc cgacaattga ctctgcgtct cttcccgctg    300
gacatcaccc tgcgccataa cctgtcccgc ggccaattcc gccaagcagt tgagcctctc    360
ctcgcaacag gctcacccct cgctgaatgg gtgacagcat tcatgggaca cacgttccga    420
accctggaac gcctgcaccc cggccatgag ggcgatgaag cccagctgag tctccacgac    480
cctgtctgtg tgtggtatgc ccttacagca gaggattcgc actggactcc ctccgccaat    540
tccccagagg acattcgtgt tgagacattg ggcc                                574

<210> SEQ ID NO 19
<211> LENGTH: 509
<212> TYPE: DNA
<213> ORGANISM: Artificial Sequence
<220> FEATURE:
<223> OTHER INFORMATION: probe

<400> SEQUENCE: 19
agacaccgca aacacctggc agcctcaggt cgctctgcac gctgtcgcaa ctctggaagc     60
tggcaacttg agctgtatcc ccgtttaccc aggctcgaca tggccgctca tcaacacccc    120
caaccgcttc caggcgtggg aaatggttca tggcaagctg ccatgggagg gtgcttttgc    180
gccggagaac aagactctcg aggccgaggg taacgatcct acctctggca accccaaccg    240
tatcgtcaag gccgctttca ggaagggtt ccccaagggc aagcccgaga acagaacatc     300
tgctgccaac ttcatggtcg agatggtgca caagtacccc ggccaggtct cgatctactc    360
tgctggagcc ctgaccaatg ttgcgctggc tgtgcgcatg gatccccagt ttgcatctct    420
ggctaaggag ttggttatca tgggtggata cgtcgatttg aatatgctcc aggccactgg    480
aagtgtcttg ctggctgatc ttcaatctg                                      509

<210> SEQ ID NO 20
<211> LENGTH: 9

```
<212> TYPE: PRT
<213> ORGANISM: Penicillium multicolor

<400> SEQUENCE: 20

Val Glu Ile Leu Leu Ile Ser Leu Thr
1               5

<210> SEQ ID NO 21
<211> LENGTH: 394
<212> TYPE: PRT
<213> ORGANISM: Penicillium multicolor

<400> SEQUENCE: 21

Val Glu Ile Leu Leu Ile Ser Leu Thr Phe Gly Asn Ile Glu Val Lys
1               5                   10                  15

Asn Cys Leu Arg Asn Val Val Ser Met Phe His Ile Leu Glu Arg Glu
                20                  25                  30

Ile Gln Trp Arg Arg Gly Asn Gly Lys Ser Glu Gly Tyr Gly Thr Met
            35                  40                  45

Arg Ala Phe Arg Pro Val Val Ala Val Gly Ala Glu Asp Pro Leu Glu
        50                  55                  60

Asp Gln Lys Met Leu Ala Asp Tyr Phe His Gly Thr Asp Gly Leu Gly
65                  70                  75                  80

Gly Ile His Ala Ser His Pro His Leu Thr Pro Ser Lys Ala Trp Glu
                85                  90                  95

His Leu Phe Thr Pro Ala Val Asp Pro Gln Gly Ile Glu Pro Val Gln
                100                 105                 110

Thr Gly Ala Gly Pro Gly Asp His Ser Phe Ile Pro Ser Arg Leu Pro
            115                 120                 125

Ala His Lys Glu Ile Leu Arg Ala Leu Arg Gln Asn Glu Pro Asp Thr
        130                 135                 140

Val Thr Leu Val Ala Val Gly Pro Leu Thr Asn Leu Ala Leu Ala Ala
145                 150                 155                 160

Ala Glu Asp Pro Glu Thr Phe Leu Arg Val Lys Glu Val Val Val Met
                165                 170                 175

Gly Gly Ala Ile Asn Gln Pro Gly Asn Val Thr Pro Val Gly Glu Phe
                180                 185                 190

Asn Ala Tyr Ala Asp Ala Val Ala Ala Arg Val Phe Ala Leu Thr
            195                 200                 205

Ser Pro Asn Pro Asn Ser Thr Leu Pro Pro Thr Thr Ser Pro Leu Leu
        210                 215                 220

Gly Leu Tyr Pro Ala Lys Leu Ser Arg Gln Leu Thr Leu Arg Leu Phe
225                 230                 235                 240

Pro Leu Asp Ile Thr Leu Arg His Asn Leu Ser Arg Gly Gln Phe Arg
                245                 250                 255

Gln Ala Val Glu Pro Leu Leu Ala Thr Gly Ser Pro Leu Ala Glu Trp
                260                 265                 270

Val Thr Ala Phe Met Gly His Thr Phe Arg Thr Leu Glu Arg Leu His
            275                 280                 285

Pro Gly His Glu Gly Asp Glu Ala Gln Leu Ser Leu His Asp Pro Val
        290                 295                 300

Cys Val Trp Tyr Ala Leu Thr Ala Glu Asp Ser His Trp Thr Pro Ser
305                 310                 315                 320

Ala Asn Ser Pro Glu Asp Ile Arg Val Glu Thr Leu Gly Gln Trp Thr
                325                 330                 335
```

```
Arg Gly Met Cys Val Ile Asp Gly Arg Asn Arg His Lys Ile Asp Gly
                340                 345                 350

Asp Glu Glu Ser Ser Ser Asp His Gly Leu Trp Leu Ser Ala Arg Ala
            355                 360                 365

Gly Asn Arg Ile Leu Arg Met Asp Gly Ser Pro Ala Glu His Thr Phe
        370                 375                 380

Gly Lys Ile Leu Ile Asp Arg Ile Phe His
385                 390

<210> SEQ ID NO 22
<211> LENGTH: 351
<212> TYPE: PRT
<213> ORGANISM: Penicillium multicolor

<400> SEQUENCE: 22

Ala Asp Lys His Tyr Ala Ile Met Asp Asn Asp Trp Tyr Thr Ala Gly
1               5                   10                  15

Phe Val Pro Tyr Leu Ile Ala Leu Asp Gly Asp Val Glu Val Leu Gly
            20                  25                  30

Leu Ala Ser Asp Thr Ala Asn Thr Trp Gln Pro Gln Val Ala Leu His
        35                  40                  45

Ala Val Ala Thr Leu Glu Ala Gly Asn Leu Ser Cys Ile Pro Val Tyr
    50                  55                  60

Pro Gly Ser Thr Trp Pro Leu Ile Asn Thr Pro Asn Arg Phe Gln Ala
65                  70                  75                  80

Trp Glu Met Val His Gly Lys Leu Pro Trp Glu Gly Ala Phe Ala Pro
                85                  90                  95

Glu Asn Lys Thr Leu Glu Ala Glu Gly Asn Asp Pro Thr Ser Gly Asn
            100                 105                 110

Pro Asn Arg Ile Val Lys Ala Ala Phe Lys Gly Phe Pro Lys Gly
        115                 120                 125

Lys Pro Glu Asn Arg Thr Ser Ala Ala Asn Phe Met Val Glu Met Val
130                 135                 140

His Lys Tyr Pro Gly Gln Val Ser Ile Tyr Ser Ala Gly Ala Leu Thr
145                 150                 155                 160

Asn Val Ala Leu Ala Val Arg Met Asp Pro Gln Phe Ala Ser Leu Ala
                165                 170                 175

Lys Glu Leu Val Ile Met Gly Gly Tyr Val Asp Leu Asn Met Leu Gln
            180                 185                 190

Ala Thr Gly Ser Val Leu Leu Ala Asp Leu Gln Ser Asp Ile Asn Leu
        195                 200                 205

Met Ile Asp Pro Glu Ala Ser Lys Ile Ala Leu Thr Ala Glu Phe Pro
210                 215                 220

Asn Ile Thr Ile Ala Gly Asn Val Ala Asn Gln Val Phe Pro Thr Lys
225                 230                 235                 240

Glu Phe Val Asp Glu Ile Ala Ser Val Pro Asn Pro Tyr Ser Lys Leu
                245                 250                 255

Phe His Asp Tyr Tyr Asp Leu Ser Phe Pro Phe Trp Asp Glu Thr Ala
            260                 265                 270

Ala Ala Leu Met Val Asp Pro Thr Leu Ala Thr Asn Gln Thr Ser Val
        275                 280                 285

Phe Leu Asp Val Asp Thr Ala Tyr Gly Ser Pro Asn Tyr Gly Asn Ile
    290                 295                 300

His Val Tyr Gln Lys Ala Leu Ala Pro Val Gly Ile Arg Glu Val Asn
305                 310                 315                 320
```

Phe Val Phe Gln Val Asp Gly Asp Arg Leu Lys Gln Arg Ile Lys His
            325                 330                 335

Ser Leu Gln Tyr Pro Lys Ser Cys Ala Asp Leu Arg Asn Glu Arg
            340                 345                 350

<210> SEQ ID NO 23
<211> LENGTH: 1185
<212> TYPE: DNA
<213> ORGANISM: Penicillium multicolor

<400> SEQUENCE: 23

| | | | | | |
|---|---|---|---|---|---|
| gttgagattc | tacttatctc | tttaacattt | ggaaacattg | aggtgaagaa | ctgtcttcga | 60 |
| aatgtggtct | ccatgtttca | tatcctcgag | cgcgagatcc | agtggcgtcg | tggtaacggc | 120 |
| aagtccgaag | gctatggcac | tatgcgtgct | ttccgcccag | tagtagccgt | gggagcggaa | 180 |
| gatcccttgg | aagaccagaa | gatgctcgct | gattatttcc | atggaaccga | tggccttggt | 240 |
| ggcatccatg | ctagtcaccc | acatctcact | ccaagcaagg | cctgggagca | tctattcacc | 300 |
| ccggccgtgg | atccccaggg | gatcgagcct | gtgcaaacgg | gagctggtcc | cggcgaccat | 360 |
| tcctttatcc | catcaagact | acctgcacac | aaggagattc | ttcgtgcact | gcgccagaat | 420 |
| gagcctgaca | ccgtgactct | cgtggcggtt | ggtccactga | ccaacttggc | cttggcagca | 480 |
| gcagaggatc | ccgaaaacct | cctacgtgtc | aaggaggtcg | ttgtgatggg | tggagcaatc | 540 |
| aaccagcctg | gaaatgtcac | ccccgttgga | gaattcaacg | cctacgcaga | cgccgttgca | 600 |
| gctgcgcgag | tctttgcgct | gacatcacct | aatcccaact | cgactctacc | accgaccacg | 660 |
| agtccactac | ttggcctgta | ccctgcaaag | ctcagccgac | aattgactct | gcgtctcttc | 720 |
| ccgctggaca | tcaccctgcg | ccataacctg | tcccgcggcc | aattccgcca | agcagttgag | 780 |
| cctctcctcg | caacaggctc | acccctcgct | gaatgggtga | cagcattcat | gggacacacg | 840 |
| ttccgaaccc | tggaacgcct | gcaccccggc | catgagggcg | atgaagccca | gctgagtctc | 900 |
| cacgaccctg | tctgtgtgtg | gtatgccctt | acagcagagg | attcgcactg | gactccctcc | 960 |
| gccaattccc | cagaggacat | tcgtgttgag | acattgggcc | agtggacgcg | tggtatgtgc | 1020 |
| gtaatcgatg | gccgaaaccg | ccataagatt | gatggcgacg | aggaaagctc | gagtgatcat | 1080 |
| ggtctgtggt | tgagtgctcg | tgcaggaaac | cgcattttgc | gaatggatgg | atcgccagcc | 1140 |
| gaacacacgt | tcggcaagat | cctcatcgat | agaatcttcc | actaa | | 1185 |

<210> SEQ ID NO 24
<211> LENGTH: 1056
<212> TYPE: DNA
<213> ORGANISM: Penicillium multicolor

<400> SEQUENCE: 24

| | | | | | |
|---|---|---|---|---|---|
| gccgacaagc | actatgccat | catggacaat | gattggtaca | cagcgggttt | cgtgccttac | 60 |
| ctgatcgccc | tcgatggcga | tgtggaggtt | ctgggcctag | cctctgacac | cgcaaacacc | 120 |
| tggcagcctc | aggtcgctct | gcacgctgtc | gcaactctgg | aagctggcaa | cttgagctgt | 180 |
| atccccgttt | acccaggctc | gacatggccg | ctcatcaaca | cccccaaccg | cttccaggcg | 240 |
| tgggaaatgg | ttcatggcaa | gctgccatgg | gagggtgctt | ttgcgccgga | gaacaagact | 300 |
| ctcgaggccg | agggtaacga | tcctacctct | ggcaacccca | accgtatcgt | caaggccgct | 360 |
| ttcaaggaag | ggttccccaa | gggcaagccc | gagaacagaa | catctgctgc | caacttcatg | 420 |
| gtcgagatgg | tgcacaagta | ccccggccag | gtctcgatct | actctgctgg | agccctgacc | 480 |

```
aatgttgcgc tggctgtgcg catggatccc cagtttgcat ctctggctaa ggagttggtt      540
atcatgggtg gatacgtcga tttgaatatg ctccaggcca ctggaagtgt cttgctggct      600
gatcttcaat ctgatatcaa cttgatgatt gatcccgagg cctccaagat cgcattgact      660
gccgaattcc ccaatatcac catcgccggt aacgtcgcca accaggtctt tcctaccaag      720
gagttcgtcg acgagatcgc ctccgttcca aaccccctaca gcaagctctt ccacgactac      780
tacgatctgt ccttcccctt ctgggatgag acggctgccg cgctgatggt tgaccctact      840
cttgctacca accagacctc tgtcttcctc gacgtggata ccgcttatgg tagccccaac      900
tatggtaaca ttcacgttta ccagaaggct cttgcccctg ttggtatccg ggaggtcaac      960
tttgtcttcc aggttgatgg ggatagactt aagcagcgca tcaagcactc tctgcagtac     1020
cccaagtcat gcgccgacct gagaaatgag cgttga                                1056
```

NUCLEOSIDASE AGENT HAVING REDUCED CONTAMINANT ACTIVITY

TECHNICAL FIELD

The present invention relates to a novel nucleosidase preparation. More particularly, the present invention relates to a nucleosidase preparation useful for reducing purine bodies in beer or beer-based beverages. The present application claims priority based on Japanese Patent Application No. 2018-022542 filed on Feb. 9, 2018, the entire contents of which are incorporated herein by reference.

BACKGROUND ART

Prevalence of hyperuricemia and gout based thereon has been on the rise due to westernization of dietary habits and increase in alcohol intake. As a cause of these diseases, purine bodies in foods or beverages have been regarded as a problem. For example, liver, milt or fish eggs, and part of fish and shellfish contain a large amount of purine bodies. Alcoholic beverages, especially brewed alcohols (beer, wine, etc.) also contain a relatively large amount of purine bodies. Alcoholic beverages are often consumed daily, and thus are considered important as risk factors for hyperuricemia and gout. For example, beer-based beverages such as beer and low-malt beer generally contain about 3 to 8 mg of purine bodies derived from raw materials (for example, malt) per 100 mL, and beer/beer-based beverages having a reduced purine body content (low-purine beer/beer-based beverages) are desired.

Attempts to reduce purine bodies in beer have been made so far. For example, in the method described in PTL 1, in the production process, an enzyme (purine nucleoside phosphorylase or nucleosidase) is caused to act on wort, thereby decomposing purine nucleoside in the wort into ribose and free purine bases. The free purine bases are assimilated by yeast during fermentation. As a result, the amount of purine bodies (free purine bases, nucleotides, and nucleosides) in beer products is reduced. PTL 2 also reports a nucleosidase useful for reducing purine bodies in beer. In addition, a method for removing purine bodies by using an adsorbent has also been proposed (PTL 3). PTL 4 also mentions that a nucleosidase can be used to reduce purine bodies in beer, and discloses that various microorganisms have nucleoside decomposition activity. PTL 5 discloses an example of a microorganism-derived nucleosidase. It is known that xanthine is the terminal substance of the purine body metabolism pathway of yeast fermentation in the production of beer, and that xanthine is increased by yeast fermentation (PTL 6).

CITATION LIST

Patent Literature

[PTL 1] JP 3824326 B
[PTL 2] JP 3824353 B
[PTL 3] JP 2004-113189 A
[PTL 4] WO 96/025483
[PTL 5] JP H10-57063 A
[PTL 6] JP 2012-125205 A

SUMMARY OF INVENTION

Technical Problem

Although various techniques for removing purine bodies in beer have been reported as described above, there is no example in which such a technique has been put into practice, and the need for techniques for producing low-purine beer is still high. With regard to beer-based beverages including low-malt beer, it is possible to reduce the purine body content by reducing the malt usage rate or by using raw materials other than malt. However, since the raw materials to be used are restricted, this cannot be said to be a fundamental solution. Accordingly, an object of the present invention is to provide an enzyme preparation useful for reducing purine bodies, especially, in beer or beer-based beverages, and use thereof.

Solution to Problem

Under the above problem, the present inventors made intensive studies to develop an enzyme preparation useful for producing low-purine beer/beer-based beverages. Purine bodies include those that can be assimilated by yeast (assimilable purine bodies) and those that cannot be assimilated thereby (non-assimilable purine bodies) in the production process. A nucleosidase can be used to reduce purine bodies in beer/beer-based beverages, but when non-assimilable purine bodies cannot be removed or when non-assimilable purine bodies are produced due to contaminant enzyme activity, the purine bodies remain in the final product (beer). Under the idea that, in order to address this problem, it is effective to suppress the production of xanthine, as one of non-assimilable purine bodies, in the production process of beer/beer-based beverages, the present inventors proceeded with the studies. As a result, the inventors succeeded in obtaining a nucleosidase preparation with a low guanine deaminase activity catalyzing the deamidation reaction to produce xanthine from guanine. When the effect of this novel nucleosidase preparation was evaluated, it was confirmed that the nucleosidase preparation is useful for reducing non-assimilable purine bodies (in other words, increasing assimilable purine bodies). The inventors also succeeded in identifying the properties of the nucleosidase preparation (level of guanine deaminase activity per nucleosidase activity) required to produce desired beer/beer-based beverages as low-purine products.

After the intensive studies as described above, the inventors succeeded in obtaining a novel nucleosidase preparation extremely useful for the production of low-purine beer/beer-based beverages. Based on this result, the following inventions are provided.

[1] A nucleosidase preparation having an activity ratio (U/U), which is guanine deaminase activity per nucleosidase activity, of 0.4 or less.

[2] The nucleosidase preparation according to [1], wherein the activity ratio is 0.36 or less.

[3] The nucleosidase preparation according to [1] or [2], which contains a nucleosidase having an amino acid sequence of SEQ ID NO: 1 or SEQ ID NO: 21 or an amino acid sequence having 85% or more identity with the amino acid sequence, or an amino acid sequence of SEQ ID NO: 2 or SEQ ID NO: 22 or an amino acid sequence having 88% or more identity with the amino acid sequence.

[4] The nucleosidase preparation according to [3], wherein the amino acid sequence of the nucleosidase is an amino acid sequence having 90% or more identity with the amino acid sequence of SEQ ID NO: 1 or SEQ ID NO: 21 or the amino acid sequence of SEQ ID NO: 2 or SEQ ID NO: 22.

[5] The nucleosidase preparation according to [1] or [2], wherein the contained nucleosidase has the following enzymological properties:

(1) action: catalyzing a reaction of hydrolyzing purine nucleosides into D-ribose and purine bases and exhibiting activity even in the presence of adenosine, adenine, inosine, hypoxanthine, guanosine, guanine, and xanthine;

(2) molecular weight: about 49 kDa (by SDS-PAGE) when the nucleosidase does not contain an N-type sugar chain;

(3) optimum temperature: 55° C. to 60° C.; and (4) thermal stability: stable at 55° C. or lower (pH 6.0, for 30 minutes).

[6] The nucleosidase preparation according to [5], wherein the contained nucleosidase further has the following enzymological properties:

(5) optimum pH: 3.5; and (6) pH stability: stable in the range of pH 3.5 to 7.5 (30° C., 30 minutes).

[7] The nucleosidase preparation according to [1] or [2], wherein the contained nucleosidase has the following enzymological properties:

(1) action: catalyzing a reaction of hydrolyzing purine nucleosides into D-ribose and purine bases and exhibiting activity even in the presence of adenosine, adenine, inosine, hypoxanthine, guanosine, guanine, and xanthine;

(2) molecular weight: about 40 kDa (by SDS-PAGE) when the nucleosidase does not contain an N-type sugar chain;

(3) optimum temperature: 50° C. to 55° C.; and (4) thermal stability: stable at 65° C. or lower (pH 4.5, for 60 minutes).

[8] The nucleosidase preparation according to [7], wherein the contained nucleosidase further has the following enzymological properties:

(5) optimum pH: 4.5; and (6) pH stability: stable in the range of pH 3.5 to 7.5 (30° C., 30 minutes).

[9] The nucleosidase preparation according to any one of [3] to [8], wherein the nucleosidase is derived from *Penicillium multicolor*.

[10] The nucleosidase preparation according to [9], wherein the *Penicillium multicolor* is an IFO 7569 strain or a mutant strain thereof.

BRIEF DESCRIPTION OF DRAWINGS

FIG. 7 Molecular weight of each purified enzyme (peaks 1 to 3). This figure also shows the results of N-terminal amino acid analysis.

FIG. 8 Probe sequences used for gene cloning. Upper: probe sequence for PN1 (SEQ ID NO: 18) and Lower: probe sequence for PN2 (SEQ ID NO: 19).

FIG. 9 Results of gene cloning. This figure shows a genomic sequence (upper, SEQ ID NO: 4) encoding the enzyme (PN1) of peak 3 and a genomic sequence (lower, SEQ ID NO: 6) encoding the enzyme (PN2) of peaks 1 and 2.

FIG. 10 Results of gene cloning. This figure shows a cDNA sequence (upper, SEQ ID NO: 3) encoding the enzyme (PN1) of peak 3 and a cDNA sequence (lower, SEQ ID NO: 5) encoding the enzyme (PN2) of peaks 1 and 2.

FIG. 11 Results of gene cloning. This figure shows the amino acid sequence of the enzyme (PN1) of peak 3 (upper, SEQ ID NO: 1) and the amino acid sequence of enzyme (PN2) of peaks 1 and 2 (lower, SEQ ID NO: 2).

FIG. 12 Results of gene cloning. The enzyme (PN1) of peak 3 and enzyme (PN2) of peaks 1 and 2 were compared in terms of the number of cDNA bases, number of introns, amino acid length, molecular weight, and estimated pI.

DESCRIPTION OF EMBODIMENTS

1. Nucleosidase Preparation

Figure 1:
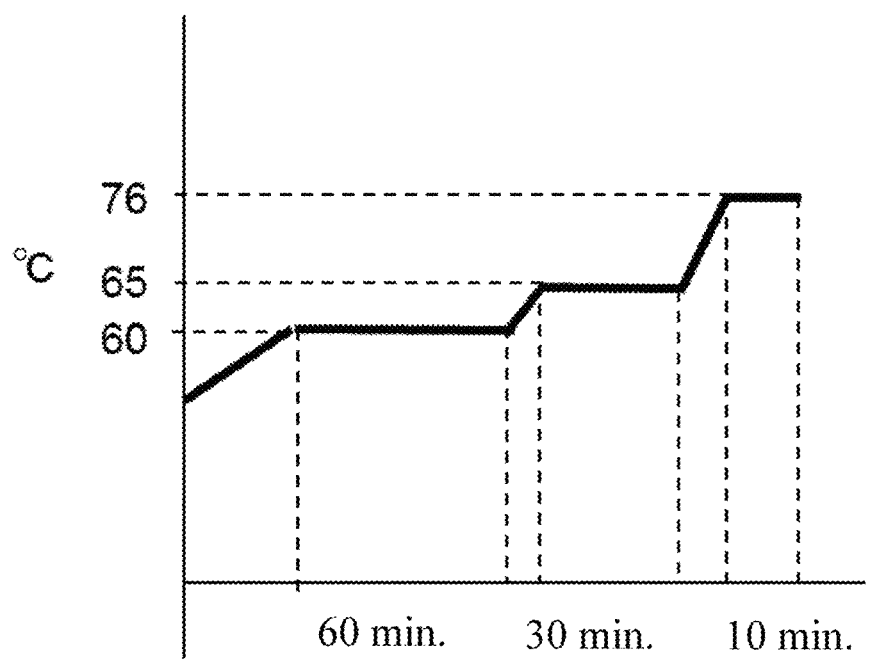
FIG. 1 Reaction process of a mashing (preparation) test.

The present invention relates to a nucleosidase preparation useful for producing low-purine beer or beer-based beverages. The "beer-based beverages" are beer-flavored beverages, and, in the present invention, are preferably fermented beverages using malt as a part of the raw materials, and more preferably fermented beverages produced by a method including the step of producing wort from malt before the fermentation step.

The main use of the nucleosidase preparation of the present invention is production of low-purine beer or beer-based beverages, but the nucleosidase preparation of the present invention can also be applied to other uses. For example, the nucleosidase preparation of the present invention may be used for the purpose of reducing purine bodies in foods or beverages other than beer or beer-based beverages. When the nucleosidase preparation of the present invention is used in the production process of foods or beverages, the purine nucleosides derived from the raw materials can be converted into free purine bases. If the free purine bases are removed in the subsequent production process, foods/beverages with a reduced content of purine bodies can be obtained. Therefore, the nucleosidase preparation of the present invention can be applied to the production of foods or beverages from which free purine bases can be removed in the production process. Examples of the corresponding foods and beverages include foods and beverages utilizing fermentation by microorganisms that can assimilate free purine bases, i.e., fermented foods and fermented beverages. Specifically, various pickles, miso, soy sauce, yogurt, fermented milk, lactic acid bacteria beverage, Shaoxing wine, and wine are exemplified. In the application of the present invention to the production of these foods and beverages, for example, the nucleosidase preparation of the present invention is added to raw materials before or during fermentation to act thereon, thereby decomposing the purine nucleosides in the raw materials into D-ribose and purine bases. The produced purine bases are typically assimilated by microorganisms during fermentation. As a result, foods or beverages having a reduced total content of purine bodies can be obtained.

The nucleosidase preparation of the present invention is characterized by having an activity ratio (U/U), which is guanine deaminase activity per nucleosidase activity, of 0.4 or less. In other words, the activity of the contaminant guanine deaminase with respect to the activity of the main ingredient nucleosidase is low.

When low-purine beer is produced using the nucleosidase preparation of the present invention, typically, the nucleosidase preparation of the present invention is added to wort to decompose the purine nucleosides in the wort into D-ribose and purine bases. It is known that the yeast used for beer fermentation usually cannot assimilate purine nucleosides, but assimilates guanine and adenine among free purine bases. Therefore, if the purine nucleosides in the wort are converted into free purine bases by the action of the nucleosidase preparation of the present invention, yeast assimilates free purine bases during the fermentation process, so that beer with a reduced total content of purine bodies is obtained (the same applies to the production of beer-based beverages).

Figure 25:
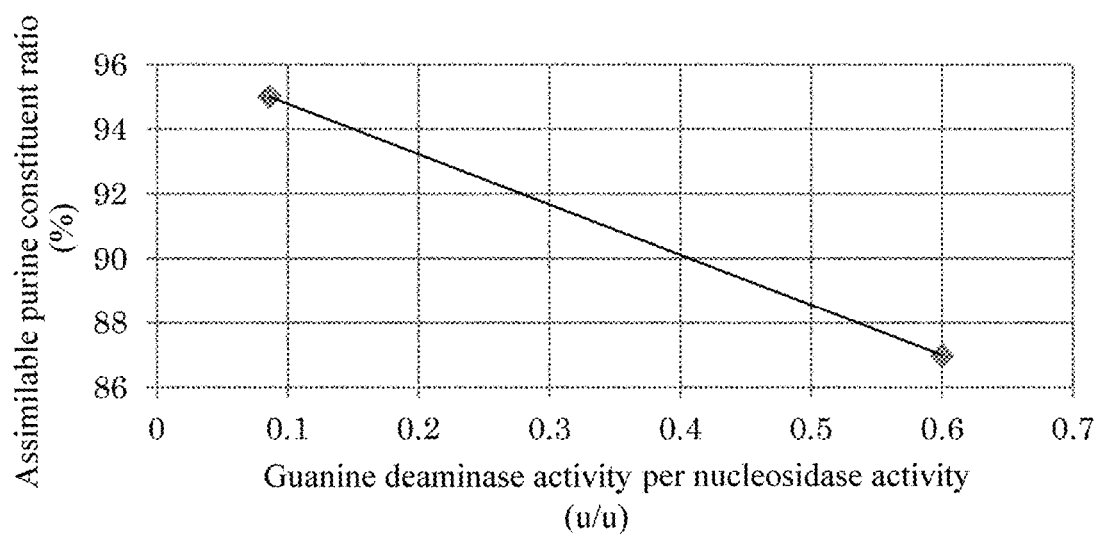
FIG. 25 Relationship between the guanine deaminase activity per nucleosidase activity and the constituent ratio of assimilable purines in the wort.

Guanine deaminase, which contaminates the nucleosidase preparation, is an enzyme that catalyzes a reaction of converting an assimilable purine, guanine, into a non-assimilable purine, xanthine. When the contaminant guanine deaminase activity is high, the amount of the non-assimilable purine (xanthine) produced is increased when the nucleosidase preparation is caused to act, leading to increase in amount of residual purine bodies in the final product (beer). Therefore, in order to obtain low-purine beer, it is desired to increase the constituent ratio of assimilable purines in the wort (ratio of assimilable purines to non-assimilable purines) using a nucleosidase preparation having a low contaminant guanine deaminase activity. The assimilable purine constituent ratio depends on the production of assimilable purines by purine nucleosidase which is the main ingredient of the nucleosidase preparation, and the production of non-assimilable purines (xanthine) by contaminant guanine deaminase. In other words, the guanine deaminase activity per nucleosidase activity (activity ratio) serves as a determinant of the assimilable purine constituent ratio. Considering the amount of residual purines in the final product (beer), it is desired that the constituent ratio of assimilable purines in the wort after the enzymatic reaction be 90% or more. It is desired that the assimilable purine constituent ratio be preferably 91% or more, more preferably 92% or more, still more preferably 93% or more, further preferably 94% or more, and most preferably 95% or more. From the experimental results shown in the Examples which will be described below, the relationship between the guanine deaminase activity per nucleosidase activity and the assimilable purine body constituent ratio is as shown in FIG. 25. In order that the assimilable purine body constituent ratio may be 90% or more, the guanine deaminase activity per nucleosidase activity needs to be 0.4 (U/U) or less. Therefore, in order to achieve the purpose, the nucleosidase preparation of the present invention is characterized by the property that "an activity ratio (U/U), which is guanine deaminase activity per nucleosidase activity, is 0.4 (U/U) or less". In order to further increase the assimilable purine constituent ratio, the guanine deaminase activity per nucleosidase activity is preferably 0.36 (U/U) or less, more preferably 0.3 (U/U) or less, even more preferably 0.2. (U/U) or less, and still further preferably 0.1 (U/U) or less.

The nucleosidase, which is the main ingredient of the nucleosidase preparation of the present invention, can be obtained by culturing a producer microorganism for the nucleosidase (nucleosidase-producer strain). Microorganisms belonging to the genera *Ochrobactrum, Streptococcus, Pediococcus, Leuconostoc, Lactobacillus, Escherichia, Citrobacter, Serratia, Alcaligenes, Flavobacterium, Bacillus, Corynebacterium, Staphylococcus, Arthrobacter, Comamonas, Pseudomonas, Kluyveromyces, Saccharomyces, Debaryomyces, Pichia, Hansenula, Sporobolomyces, Sporidiobolus, Aspergillus, Penicillium*, and the like can be adopted as the nucleosidase-producer strain. The nucleosidase-producer strain may be a wild strain or a mutant strain (a mutant strain can be obtained, for example, by ultraviolet irradiation). Specific examples of the nucleosidase-producer strain include *Ochrobactrum anthropi* (FERM BP-5377), *Streptococcus citrovorum, Pediococcus pentosaceus* (IFO 3182), *Leuconostoc dextranicum, Lactobacillus plantarum* (*Lactobacillus arabinosus*) (IFO 3070), *Lactobacillus plantarum* (*Lactobacillus cucumeris*) (IFO 3074), *Escherichiacoli* B biotin less, *Citrobacter freundii* (IFO 13546), *Serratia marcescens* (IFO 3736), *Alcaligenes faecalis, Flavobacterium meningosepticum* (DSM2800), *Bacillus cereus, Corynebacterium glutamicum* (ATCC13060), *Staphylococcus aureus* (IFO 3060), *Arthrobacter ureafaciens, Arthrobacter globiformis*) (IFO 12140), *Comamonas testosteroni* (*Pseudomonas dacunhae*) (IFO 12048), *Pseudomonas putida, Bacillus aneurinolyticus, Bacillus thuringiensis* (IFO 3951), *Kluyveromyces marxianus, Saccharomyces maxianus* (IFO 0277), *Debaryomyces pseudopolymorphus* (*Pichia pseudopolymorpha*) (IFO 1026), *Pichia capsulata* (*Hansenula capsulata*) (IFO 0721), *Sporobolomyces salmonicolor* (IFO 1038), *Sporidiobulus salmonicolor* (*Sporobolomyces odorus*) (IFO 1035), *Aspergillus niger* (IFO 4416), *Penicillium spinulosum* (IAM 7047), *Aspergillus awamori* (IFO 4033), *Aspergillus oryzae* (IAM 2630), *Aspergillus flavus* (IFO 5839), *Aspergillus terreus* (IFO 5445), *Aspergillus sojae* (IFO 4386), *Aspergillus parasiticus* (IFO 4082), and *Penicillium* sp. A host microorganism into which a nucleosidase gene acquired from the nucleosidase-producer strain (or a gene obtained by modifying the gene) has been introduced can also be used as the nucleosidase-producer strain.

When the contaminant guanine deaminase activity of the nucleosidase acquired from the producer strain is high, for example, various chromatographies (ion exchange chromatography, hydrophobic chromatography, affinity chromatography, etc.), heat treatment, pH treatment, salting-out, and the like may appropriately be combined for purification to thereby reduce the contaminant guanine deaminase activity to a required level. It is also possible to subject the producer strain to mutation treatment (irradiation with ultraviolet rays, X rays, or γ rays, treatment with nitrous acid, hydroxylamine, N-methyl-N'-nitro-N-nitrosoguanidine, etc.), thereby obtaining a mutant strain having a low contaminant guanine deaminase activity per nucleosidase activity. The "contaminant guanine deaminase activity per nucleosidase activity" that serves as an index can be evaluated by the method which will be described below.

Preferably, the nucleosidase preparation of the present invention is composed mainly of a nucleosidase derived from *Penicillium multicolor*. The "nucleosidase derived from *Penicillium multicolor*" means a nucleosidase produced by a microorganism (which may be a wild strain or a mutant strain) classified as *Penicillium multicolor*, or a nucleosidase obtained by a genetic engineering technique using a nucleosidase gene of *Penicillium multicolor* (which may be a wild strain or a mutant strain). Therefore, a recombinant produced by a host microorganism into which a nucleosidase gene acquired from *Penicillium multicolor* (or a gene obtained by modifying the gene) has been introduced is also included in the "nucleosidase derived from *Penicillium multicolor*".

Particularly preferably, the nucleosidase that constitutes the nucleosidase preparation of the present invention is either of two types of nucleosidases acquired from *Penicillium multicolor* (hereinafter, referred to as "PN1" and "PN2", in correspondence with the indications in the Examples) (which may also be an equivalent thereof). In one embodiment, both of these two nucleosidases (which may also be equivalents thereof) are included in the nucleosidase preparation of the present invention. The equivalent herein is an enzyme having an equivalent amino acid sequence and exhibiting an equivalent function (specifically, enzyme activity). The amino acid sequence of PN1 is shown in SEQ ID NO: 1, and the amino acid sequence of PN2 is shown in SEQ ID NO: 2. The amino acid sequence of a mature form of PN1 is shown in SEQ ID NO: 21, and the amino acid sequence of a mature form of PN2 is shown in SEQ ID NO: 22. The nucleosidase which constitutes the nucleosidase preparation of a preferred embodiment has an amino acid sequence of SEQ ID NO: 1 or an amino acid sequence of SEQ ID NO: 21, or an amino acid sequence of SEQ ID NO: 2 or an amino acid sequence of SEQ ID NO: 22, or an amino acid sequence equivalent to any of these amino acid sequences. The "equivalent amino acid sequence" refers to an amino acid sequence which is partially different from the reference sequence (amino acid sequence of SEQ ID NO: 1, amino acid sequence of SEQ ID NO: 21, amino acid sequence of SEQ ID NO: 2, or amino acid sequence of SEQ ID NO: 22), but in which the difference does not substantially affect the function (nucleosidase activity) of the protein. Therefore, the enzyme having the polypeptide chain consisting of the equivalent amino acid sequence exhibits nucleosidase activity. The degree of activity is not particularly limited as long as the function as a nucleosidase can be exerted. However, it is preferable that the activity be equivalent to or higher than that of the enzyme having the polypeptide chain consisting of the reference sequence.

The term "partial difference in the amino acid sequence" typically means mutation (change) in the amino acid sequence caused by deletion or substitution of one to several (up to, for example, 3, 5, 7, or 10) amino acids composing the amino acid sequence, or addition, insertion, or combination thereof of one to several (up to, for example, 3, 5, 7, or 10) amino acids. The difference in the amino acid sequence is acceptable as long as the nucleosidase activity is maintained (the activity may be varied to a degree). As long as the conditions are satisfied, the position of the difference in the amino acid sequence is not particularly limited, and the difference may arise in a plurality of positions. As to the amino acid sequence of SEQ ID NO:1 or SEQ ID NO:21, the term "plurality" means, for example, a number corresponding to less than about 15%, preferably less than about 10%, more preferably less than about 5%, even more preferably less than about 3% of the total amino acids, and most preferably less than about 1%. As to the amino acid sequence of SEQ ID NO:2 of SEQ ID NO:22, the term "plurality" means, for example, a number corresponding to less than about 12%, preferably less than about 10%, more preferably less than about 5%, even more preferably less than about 3% of the total amino acids, and most preferably less than about 1%. More specifically, in a case where the amino acid sequence of SEQ ID NO:1 or SEQ ID NO:21 is the reference amino acid sequence, the equivalent protein has, for example, about 85% or more, preferably about 90% or more, more preferably about 95% or more, much more preferably about 98% or more, and most preferably about 99% or more identity with the reference amino acid sequence, whereas in a case where the amino acid sequence of SEQ ID NO:2 or SEQ ID NO:22 is the reference amino acid sequence, the equivalent protein has, for example, about 88% or more, preferably about 90% or more, more preferably about 95% or more, much more preferably about 98% or more, and most preferably about 99% or more identity with the reference amino acid sequence. The difference of the amino acid sequence may arise in a plurality of positions.

Preferably, the equivalence protein is obtained by causing conservative amino acid substitution in an amino acid residue which is not essential for nucleosidase activity. The term "conservative amino acid substitution" means the substitution of an amino acid residue with another amino acid residue having a side chain with similar properties. Amino acid residues are classified into several families according to their side chains, such as basic side chains (for example, lysine, arginine, and histidine), acidic side chains (for example, aspartic acid and glutamic acid), uncharged polar side chains (for example, glycine, asparagine, glutamine, serine, threonine, tyrosine, and cysteine), nonpolar side chains (for example, alanine, valine, leucine, isoleucine, proline, phenylalanine, methionine, and tryptophan), β branched side chains (for example, threonine, valine, and isoleucine), and aromatic side chains (for example, tyrosine, phenylalanine, tryptophan, and histidine). Conservative amino acid substitution is preferably the substitution between amino acid residues in one family.

The identity (%) between two amino acid sequences or two nucleic acid sequences (hereinafter, the term "two sequences" are used for representing either of two sequences) can be determined by the following procedure. Firstly, two sequences are aligned for optimum comparison of the two sequences (for example, a gap may be introduced into the first sequence so as to optimize the alignment with respect to the second sequence). When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions×100). Preferably, the number and size of the gaps, which are required to optimize the alignment of the two sequences, are taken into consideration.

The comparison and determination of the identity between two sequences can be carried out by using a mathematical algorithm. A specific example of the mathematical algorithm that can be used for comparing the sequences includes an algorithm described in Karlin and Altschul (1990) Proc. Natl. Acad. Sci. USA 87:2264-68 and modified by Karlin and Altschul (1993) Proc. Natl. Acad. Sci. USA 90:5873-77. However, the algorithm is not necessarily limited to this. Such an algorithm is incorporated in NBLAST program and XBLAST program (version 2.0) described in Altschul et al. (1990) J. Mol. Biol. 215: 403-10. In order to obtain an equivalent nucleic acid sequence, for example, BLAST nucleotide search with score=100 and word length=12 may be carried out by the NBLAST program. In order to obtain an equivalent amino acid sequence, for example, BLAST polypeptide search with score=50 and word length=3 may be carried out by the XBLAST program. In order to obtain gapped alignments for comparison, Gapped BLAST described in Altschul et al., (1997) Amino Acids Research 25(17): 3389-3402 can be utilized. In using BLAST and Gapped BLAST, the default parameters of the corresponding programs (e.g., XBLAST and NBLAST) can be used. In detail, see http://www.ncbi.nlm.nih.gov. Another example of the mathematical algorithm that can be used for comparing sequences includes an algorithm described in Meyers and Miller (1988) Comput. Appl. Biosci. 4: 11-17. Such programs are incorporated into the ALIGN program that can be used for, for example, GENESTREAM network server (IGH Montpellier, France) or ISREC server. When the ALIGN program is used for comparison of the amino acid sequences, for example, PAM120 weight residue table can be used in which a gap length penalty is 12 and a gap penalty is 4.

The identity between two amino acid sequences can be determined by using the GAP program in the GCG software package, using Blossom 62 matrix or PAM250 matrix with the gap weight of 12, 10, 8, 6, or 4, and the gap length weight of 2, 3, or 4. The identity between two nucleic acid sequences can be determined by using the GAP program in the GCG software package (available at http://www.gcg.com), with the gap weight of 50, and the gap length weight of 3.

The nucleosidase which composes the nucleosidase preparation of the present invention may be a portion of a larger protein (for example, a fused protein). Examples of the sequence added to a fused protein include the sequences useful for purification of multiple histidine residues, and addition sequences which ensures stability in recombination production.

The nucleosidase having the above-described amino acid sequence is readily prepared by a genetic engineering technique. For example, an appropriate host cell (for example, *Escherichia coli*) is transformed by a DNA encoding the nucleosidase, and the protein expressed in the transformant is collected, and thereby preparing the present enzyme. The collected protein is treated as appropriate according to the intended use. The present enzyme thus obtained as a recombinant protein may be subjected to various modifications. For example, the present enzyme composed of a recombinant protein linked to any peptide or protein can be obtained by producing a recombinant protein using a vector into which a DNA encoding the present enzyme has been inserted together with other appropriate DNA. In addition, modification for causing addition of a sugar chain and/or a lipid, or N- or C-terminal processing may be carried out. These modifications allow, for example, extraction of a recombinant protein, simplification of purification, or addition of biological functions.

PN1 and PN2 can also be characterized by the following enzymological properties.

<Enzymological Properties of PN1>

(1) Action

PN1 is a nucleosidase and catalyzes a reaction of hydrolyzing purine nucleosides into D-ribose and purine bases. The purine nucleoside is a glycoside in which a purine base and a reducing group of sugar are bound by an N-glycoside bond. Examples of the purine nucleoside include adenosine, guanosine, and inosine. In addition, the purine base is a generic term for bases having a purine skeleton, and specific examples thereof include adenine, guanine, hypoxanthine, and xanthine. In addition to purine nucleosides and purine bases, compounds having a purine skeleton including purine nucleotides and the like are collectively referred to as purine bodies.

PN1 shows activity even in the presence of adenosine, adenine, inosine, hypoxanthine, guanosine, guanine, and xanthine. In other words, PN1 is not subject to substantial inhibition by decomposition products. This characteristic feature is particularly important in applying the present enzymes to the production of foods and beverages. According to PN1 exhibiting this characteristic feature, it is possible to efficiently decompose the purine nucleosides derived from the raw materials in the production process of foods and beverages.

(2) Molecular Weight

PN1 contains a sugar chain (i.e., PN1 is a glycoprotein) in its natural form, and the molecular weight before removal of N-linked oligosaccharides was about 53 kDa (molecular weight measured by SDS-PAGE). The molecular weight is about 126 kDa when measured by gel filtration chromatography, and PN1 is presumed to form a dimer. On the other hand, the molecular weight, when measured by SDS-PAGE after removal of N-linked oligosaccharides, was about 49 kDa. Therefore, the molecular weight of the present enzyme when not containing N-linked oligosaccharides is about 49 kDa (molecular weight measured by SDS-PAGE).

(3) Optimum Temperature

The optimum temperature of PN1 is 55° C. to 60° C. This high optimum temperature as described above is advantageous in the application of PN1 to the production of foods and beverages through a treatment process at a relatively high temperature. The optimum temperature can be evaluated by using an acetate buffer (pH 4.3) and also using guanosine as a substrate for quantitating the reaction product ribose.

(4) Thermal Stability

When treated in an acetate buffer (pH 4.5) for 60 minutes, PN1 maintains 80% or more activity under temperature conditions of 45° C. or lower. Therefore, for example, when the temperature during treatment is in the range of 5° C. to 45° C., the residual activity after the treatment becomes 80% or more.

On the other hand, when PN1 is treated in a phosphate buffer (pH 6.0) for 30 minutes, PN1 maintains 80% or more activity under the temperature conditions of 55° C. or lower. Therefore, for example, when the temperature during treatment is in the range of 5° C. to 55° C., the residual activity after the treatment becomes 80% or more.

PN1 which exhibits such excellent thermal stability can show high activity even under relatively high temperature conditions, for example, in the beer preparation process.

PN1 can be further characterized by the following enzymological properties (5) and (6).

(5) Optimum pH

The optimum pH of PN1 is 3.5. The optimum pH is determined based on the measurement results, for example, in a citrate buffer for the pH range of 2.5 to 3.5, in an acetate buffer for the pH range of 3.5 to 5.5, and in a potassium phosphate buffer for the pH range of 5.5 to 6.5.

(6) pH Stability

PN1 shows stable activity in a wide pH range. For example, if the pH of the enzyme solution to be treated is within the range of 3.5 to 7.5, PN1 shows 80% or more of the maximum activity after treatment at 30° C. for 30 minutes. Also, in the case of the treatment at 50° C. for 60 minutes, if the pH of the enzyme solution to be treated is within the range of 3.5 to 7.5, PN1 shows 80% or more of the maximum activity after the treatment. The pH stability is determined based on the measurement results, for example, in a citrate buffer for the pH range of 2.5 to 3.5, in an acetate buffer for the pH range of 3.5 to 5.5, and in a potassium phosphate buffer for the pH range of 5.5 to 6.5.

<Enzymological Properties of PN2>

(1) Action

PN2 is a nucleosidase and catalyzes a reaction of hydrolyzing purine nucleosides into D-ribose and purine bases.

PN2 also shows activity in the presence of adenosine, adenine, inosine, hypoxanthine, guanosine, guanine, and xanthine. In other words, PN2 is not subject to substantial inhibition by decomposition products. This characteristic feature is particularly important in applying the present enzymes to the production of foods and beverages. According to PN2 exhibiting this characteristic feature, it is possible to efficiently decompose the purine nucleosides derived from the raw materials in the production process of foods and beverages.

(2) Molecular Weight

PN2 contains a sugar chain (i.e., PN2 is a glycoprotein) in its natural form, and the molecular weight before removal of N-linked oligosaccharides was about 51 kDa (molecular weight measured by SDS-PAGE). The molecular weight was about 230 kDa when measured by gel filtration chromatography. On the other hand, the molecular weight, when measured by SDS-PAGE after removal of N-linked oligosaccharides, was about 40 kDa. Therefore, the molecular weight of the present enzyme when not containing N-linked oligosaccharides is about 40 kDa (molecular weight measured by SDS-PAGE).

(3) Optimum Temperature

The optimum temperature of PN2 is 50° C. to 55° C. This high optimum temperature as described above is advantageous in the application of PN2 to the production of foods and beverages through a treatment process at a relatively high temperature. The optimum temperature can be evaluated by using an acetate buffer (pH 4.3) and also using guanosine as a substrate for quantitating the reaction product ribose.

(4) Thermal Stability

When treated in an acetate buffer (pH 4.5) for 60 minutes, PN2 maintains 80% or more activity under temperature conditions of 65° C. or lower. Therefore, for example, when the temperature during treatment is in the range of 5° C. to 65° C., the residual activity after the treatment becomes 80% or more.

On the other hand, when treated in a phosphate buffer (pH 6.0) for 30 minutes, PN2 maintains 80% or more activity under the temperature conditions of 55° C. or lower. Therefore, for example, when the temperature during treatment is in the range of 5° C. to 55° C., the residual activity after the treatment becomes 80% or more.

PN2 which exhibits such excellent thermal stability can show high activity even under relatively high temperature conditions, for example, in the beer preparation process.

PN2 can be further characterized by the following enzymological properties (5) and (6).

(5) Optimum pH

The optimum pH of PN2 is 4.5. The optimum pH is determined based on the measurement results, for example, in a citrate buffer for the pH range of 2.5 to 3.5, in an acetate buffer for the pH range of 3.5 to 5.5, and in a potassium phosphate buffer for the pH range of 5.5 to 6.5.

(6) pH Stability

PN2 shows stable activity in a wide pH range. For example, if the pH of the enzyme solution to be treated is within the range of 3.5 to 7.5, PN2 shows 80% or more of the maximum activity after treatment at 30° C. for 30 minutes. In addition, in the case of the treatment at 50° C. for 60 minutes, if the pH of the enzyme solution to be treated is within the range of 4.5 to 7.5, PN2 shows 80% or more of the maximum activity, after the treatment. The pH stability is determined based on the measurement results, for example, in a citrate buffer for the pH range of 2.5 to 3.5, in an acetate buffer for the pH range of 3.5 to 5.5, and in a potassium phosphate buffer for the pH range of 5.5 to 6.5.

As shown in Examples described below, the present inventors have succeeded in isolating and purifying nucleosidases having the above properties from a *Penicillium multicolor* IFO 7569 strain. The *Penicillium multicolor* IFO 7569 strain is a bacterial strain (published as NBRC 7569 in the NBRC Culture catalog) stored in the National Institute of Technology and Evaluation (2-5-8 Kazusakamatari, Kisarazu, Chiba), and can be obtained through prescribed procedures.

The content of the nucleosidase in the nucleosidase preparation of the present invention is not particularly limited. For example, 100 U to 100,000 U of the nucleosidase is contained per g of the nucleosidase preparation. The nucleosidase preparation of the present invention may be in a liquid form or a solid form (including a powder form). The nucleosidase preparation of the present invention may contain an excipient, a buffer agent, a suspending agent, a stabilizer, a preservative, an antiseptic, saline, and the like besides the active ingredient (i.e. the present enzyme). As the excipient, lactose, sorbitol, D-mannitol, maltodextrin, white soft sugar, and the like can be used. As the buffer agent, phosphates, citrates, acetates, and the like can be used. As the stabilizer, propylene glycol, ascorbic acid, and the like can be used. As the preservative, phenol, benzalkonium chloride, benzyl alcohol, chlorobutanol, methylparaben, and the like can be used. As the antiseptic, benzalkonium chloride, paraoxybenzoic acid, chlorobutanol, and the like can be used.

2. Method for Producing Nucleosidase Preparation

The nucleosidase preparation of the present invention can be obtained by a method characterized in that the step of culturing a producer microorganism for the nucleosidase (step (1)) and the step of collecting the nucleosidase from the culture solution and/or the cell bodies after culture (step (2)) are carried out. The producer microorganism for the nucleosidase is, for example, *Penicillium multicolor*, preferably a *Penicillium multicolor* IFO 7569 strain or a mutant strain thereof. The mutant strain can be obtained, for example, by irradiation with ultraviolet rays, X rays, γ rays, or the like, or treatment with nitrous acid, hydroxylamine, N-methyl-N'-nitro-N-nitrosoguanidine, or the like.

Conditions and methods for culturing cells are not particularly limited, as long as the nucleosidase is produced. Thus, methods and culture conditions that are suitable for culturing a microorganism to be used can be set as appropriate, with the proviso that the nucleosidase is produced. Although the culturing may be by either liquid culture or solid culture, liquid culture is preferably employed. Taking liquid culture as an example, culturing conditions therefor will be described below.

As the medium, any medium can be used as long as microorganisms to be used can grow. For example, a medium supplemented with a carbon source such as glucose, sucrose, gentiobiose, soluble starch, glycerin, dextrin, molasses, and organic acid; and further, a nitrogen source such as ammonium sulfate, ammonium carbonate, ammonium phosphate, ammonium acetate, or peptone, yeast extract, corn steep liquor, casein hydrolysate, bran, and meat extract; and furthermore, an inorganic salt such as potassium salt, magnesium salt, sodium salt, phosphate salt, manganese salt, iron salt, and zinc salt, and the like, can be used. In order to promote the growth of transformants to be used, vitamin, amino acid, and the like, may be added to the medium. The medium is cultured under the aerobic conditions such that the pH of the medium is adjusted to, for example, about 3 to 8 (preferably about 4 to 7), and the culture temperature is generally about 20° C. to 40° C. (preferably about 25° C. to 35° C.) for 1 to 20 days (preferably 3 to 10 days). An example of the culture method may include a shake culture method, and an aerobic submerged culture method by using a jar fermenter.

After culturing under the above conditions, the target enzyme (nucleosidase) is collected from the culture solution or the cell bodies (step (2)). When it is collected from the culture solution, the nucleosidase can be obtained by separation and purification by removing insoluble matters by, for example, filtration of culture supernatant, centrifugation, and the like, followed by carrying out, for example, concentration by ultrafiltration membrane, salting out by ammonium sulfate precipitation, dialysis, various types of chromatography of an ion-exchange resin or an appropriate combination thereof. On the other hand, when it is collected from cell bodies, the nucleosidase can be obtained by pulverizing the cell bodies by pressuring treatment, ultrasonic treatment, or the like, followed by separation and purification thereof similar to the above. After collection of the cell bodies from a culture solution by filtration, centrifugation, etc., a series of processes (pulverizing, separation, and purification of cell bodies) mentioned above may be carried out.

In one embodiment, in order to obtain a liquid nucleosidase preparation through simple operations, an enzyme preparation is produced by a production method including the following steps (I) and (II):

(I) culturing a producer microorganism for the nucleosidase; and (II) removing the cell bodies after culture.

Step (I) is similar to the above step (1), and thus the explanation thereof will be omitted. In step (II) following step (I), the cell bodies are removed by centrifugation, filtration, filter treatment, or the like. The thus-obtained culture solution containing no cell body is used as a nucleosidase preparation as it is or after further treatment (i.e., the step (step (III)) of purifying the culture solution after removing the cell bodies).

The nucleosidase preparation can also be produced using a recombinant bacterium into which a nucleosidase gene has been introduced. When the nucleosidase preparation is produced using a recombinant bacterium, a nucleosidase gene is introduced into an appropriate host microorganism to obtain a recombinant bacterium (transformant), and then the transformant is cultured under the condition that the protein encoded by the gene introduced into the host microorganism is produced (step (i)). Conditions for culturing the transformant are known for various vector host systems, and those skilled in the art can easily set appropriate culture conditions. Following the culture step, the produced protein (i.e., nucleosidase) is collected (step (ii)). The collection and the subsequent purification may be performed in the same manner as in the case of the above embodiment.

As the nucleosidase gene, preferably, a gene containing the DNA encoding the amino acid sequence of SEQ ID NO: 1 (DNA encoding PN1), the DNA encoding the amino acid sequence of SEQ ID NO: 21 (DNA encoding the mature form of PN1), the DNA encoding the amino acid sequence of SEQ ID NO: 2 (DNA encoding PN2), or the DNA encoding the amino acid sequence of SEQ ID NO: 22 (DNA encoding the mature form of PN2) is used. Specific examples of the embodiment include the DNA consisting of a base sequence of SEQ ID NO: 3 (corresponding to the cDNA encoding the amino acid sequence of SEQ ID NO: 1), the DNA consisting of a base sequence of SEQ ID NO: 23 (corresponding to the cDNA encoding the amino acid sequence of SEQ ID NO: 21), the DNA consisting of a base sequence of SEQ ID NO: 4 (corresponding to the genomic DNA encoding the amino acid sequence of SEQ ID NO: 1), the DNA consisting of a base sequence of SEQ ID NO: 5 (corresponding to the cDNA encoding the amino acid sequence of SEQ ID NO: 2), the DNA consisting of a base sequence of SEQ ID NO: 24 (corresponding to the cDNA encoding the amino acid sequence of SEQ ID NO: 22), and the DNA consisting of a base sequence of SEQ ID NO: 6 (corresponding to the genomic DNA encoding the amino acid sequence of SEQ ID NO: 2).

The gene of the nucleosidase can be prepared in an isolated state by using a standard genetic engineering technique, a molecular biological technique, a biochemical technique, a chemical synthesis, a PCR method (e.g. an overlap extension PCR) or a combination thereof, with reference to sequence information disclosed in the present specification or attached sequence list.

In general, when a part of DNA encoding a certain protein is modified, a protein encoded by the modified DNA may sometimes have the equal function to that of a protein encoded by the DNA before modification. That is to say, the modification of the DNA sequence does not have a substantial effect on the function of the encoded protein, so that the function of the encoded protein may be maintained before and after the modification. Thus, as another embodiment, the present invention provides DNA encoding a protein having a base sequence equivalent to the reference base sequence (i.e., any one of SEQ ID NOs: 3 to 6, 23 and 24) and having the nucleosidase activity (hereinafter, which is also referred to as "equivalent DNA"). The "equivalent base sequence"

herein denotes a base sequence which is partly different from the reference base sequence but in which the function (herein, nucleosidase activity) of the protein encoded by the sequence is not substantially affected by the difference.

A specific example of the equivalent DNA includes DNA that hybridizes to the complementary base sequence of the reference base sequence under stringent conditions. Herein, the "stringent conditions" are referred to as conditions in which a so-called specific hybrid is formed but a nonspecific hybrid is not formed. Such stringent conditions are known to persons skilled in the art. Such stringent conditions can be set with reference to, for example, Molecular Cloning (Third Edition, Cold Spring Harbor Laboratory Press, New York) and Current protocols in molecular biology (edited by Frederick M. Ausubel et al., 1987). An example of the stringent conditions can include a condition in which a hybridization solution (50% formamide, 10×SSC (0.15 M NaCl, 15 mM sodium citrate, pH 7.0), 5×Denhardt solution, 1% SDS, 10% dextran sulfate, 10 µg/ml denatured salmon sperm DNA, and 50 mM phosphate buffer (pH 7.5)) is used and incubated at about 42° C. to about 50° C., thereafter, washed with 0.1×SSC and 0.1% SDS at about 65° C. to about 70° C. Further preferable stringent conditions can include, for example, a condition in which a hybridization solution 50% formamide, 5×SSC (0.15 M NaCl, 15 mM sodium citrate, pH 7.0), 1×Denhardt solution, 1% SDS, 10% dextran sulfate, 10 µg/ml denatured salmon sperm DNA, and 50 mM phosphate buffer (pH 7.5)) is used.

Another specific example of the equivalent DNA can include DNA encoding a protein having a base sequence which includes substitution, deletion, insertion, addition or inversion in one or a plurality of bases (preferably one to several bases) in the reference base sequence, and which has a β-galactosidase activity. The substitution, deletion, or the like, of the base may occur in a plurality of sites. The "plurality" herein denotes, for example, 2 to 40 bases, preferably 2 to 20 bases, and more preferably 2 to 10 bases, although it depends upon the positions or types of the amino acid residue in the three-dimensional structure of the protein encoded by the DNA.

The equivalent DNA shows a 70% or more identity for example, preferably a 80% or more identity, more preferably a 90% or more identity, more and more preferably a 95% or more identity, and most preferably a 99% or more identity with the reference base sequence (i.e., any one of SEQ ID NOs: 3 to 6, 23 and 24).

The above-mentioned equivalent DNA can be obtained by modifying the reference DNA so as to include substitution, deletion, insertion, addition and/or inversion of base by using treatment with a restriction enzyme; treatment with exonuclease, DNA ligase, etc; introduction of mutation by a site-directed mutagenesis (Molecular Cloning, Third Edition, Chapter 13, Cold Spring Harbor Laboratory Press, New York) and random mutagenesis (Molecular Cloning, Third Edition, Chapter 13, Cold Spring Harbor Laboratory Press, New York), and the like. Furthermore, the equivalent DNA can be also obtained by other methods such as irradiation with ultraviolet ray. A further example of the equivalent DNA can include DNA having difference in base as mentioned above due to polymorphism represented by SNP (single nucleotide polymorphism).

In order to obtain a recombinant bacterium into which the nucleosidase gene has been introduced, typically, an expression vector containing the nucleosidase gene is constructed, and the host cell is transformed with the expression vector. An appropriate vector is selected in consideration of the type of host cell. As a vector using *E. coli* as a host, M13 phage or a modified form thereof, λ phage or a modified form thereof, pBR322 or a modified form thereof (pB325, pAT153, pUC8, etc.), or the like can be exemplified. As a vector using yeast as a host, pYepSec1, pMFa, pYES2, or the like can be exemplified. As a vector using an insect cell as a host, pAc, pVL, or the like can be exemplified. As a vector using a mammalian cell as a host, pCDM8, pMT2PC, or the like can be exemplified.

The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of DNA into the vector, insertion of a selective marker gene (if necessary), insertion of a promoter (if necessary), and the like can be performed by using a standard recombinant DNA technique (for example, a known method of using a restriction enzyme and a DNA ligase, which can be referred in Molecular Cloning, Third Edition, 1.84, Cold Spring Harbor Laboratory Press, New York).

For the preparation of the transformant by using the above expression vector, transfection or transformation can be used. The transfection and transformation can be carried out by, for example, a calcium phosphate coprecipitation method, electroporation (Potter, H. et al., Proc. Natl. Acad. Sci. U.S.A. 81, 7161-7165(1984)), lipofection (Feigner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73, 366-370 (1976)), a method by Hanahan (Hanahan, D., J. Mol. Biol. 166, 557-580 (1983)), a lithium acetate method (Schiestl, R. H. et al., Curr. Genet. 16, 339-346 (1989)), protoplast-polyethylene glycol method (Yelton, M. M. et al., Proc. Natl. Acad. Sci. 81, 1470-1474 (1984)), and the like.

The host cell is not particularly limited as long as the nucleosidase can be expressed, and it can be selected from, for example, *Bacillus* genus bacteria (e.g. *Bacillus subtillis, Bacillus licheniformis, Bacillus circulans*, etc.), lactic acid bacteria (e.g. *Lactococcus, Lactobacillus, Streptococcus, Leuconostoc, Bifidobacterium*, etc.), other bacteria (e.g. *Escherichia, Streptomyces*, etc.), yeast (e.g. *Saccharomyces, Kluyveromyces, Candida, Torula, Torulopsis*, etc.), and filamentous fungi (*Eumycetes*) (e.g. *Aspergillus* genus fungi such as *Aspergillus oryzae* and *Aspergillus niger, Penicillium* genus fungi, *Trichoderma* genus fungi, *Fusarium* genus fungi, etc.).

EXAMPLES

Example 1 Acquisition and Identification of Novel Nucleosidase

1. Acquisition of Novel Nucleosidase

More than 10,000 kinds of microorganisms were screened in order to find an enzyme useful for producing low-purine beer. As a result, four strains of microorganisms, i.e., a *Penicillium multicolor* IFO 7569 strain, a *Bacillus brevis* IFO 15304 strain, a *Brevibacillus linens* IFO 12141 strain, and a *Mucor javanicus* 4068 strain were identified as promising candidates. Assuming that the nucleosidases produced by these microorganisms were used in the beer preparation process, the nucleosidases were evaluated in terms of the action and effect under general conditions (mashing test) for the preparation process. As a result of re-examination, the *Penicillium multicolor* IFO 7569 strain was identified as a *Penicillium maximae*.

(1) Method for Culturing *Penicillium multicolor* IFO 7569 Strain

A *Penicillium multicolor* IFO 7569 strain was inoculated into 100 mL of the following culture medium B and cultured with shaking in a Sakaguchi flask with a volume of 500 mL at 27° C. for 48 to 72 hours. This preculture solution was transferred to 2 L of the following culture medium B and cultured with aeration and agitation at 27° C. for 120 to 188 hours. This culture solution was filtered through diatomaceous earth to remove cell bodies. The culture supernatant obtained after removal of the cell bodies was concentrated with an ultrafiltration membrane to obtain lyophilized powders.

<Culture Medium A>
1% Lustergen FK (Nippon Starch Chemical Co., Ltd.)
1% Yeast extract (Difco)
0.5% NaCl
pH 7.0
<Culture Medium B>
1% Lustergen FK (Nippon Starch Chemical Co., Ltd.)
1% Yeast extract (Difco)
2% Cornmeal (Matsumoto Nosan K.K.)
0.5% NaCl
pH 6.5

(2) Method for Culturing *Bacillus brevis* IFO 15304 Strain, *Brevibacillus linens* IFO 12141 Strain, and *Mucor javanicus* 4068 Strain A *Bacillus brevis* IFO 15304 strain and a *Brevibacillus linens* IFO 12141 strain were each inoculated into 10 mL of the above culture medium A and cultured with shaking at 30° C. for 48 hours in a test tube. On the other hand, a *Mucor javanicus* IFO 4068 strain was inoculated into the above culture medium B 10 mL and cultured under the same conditions. The culture solutions were each transferred to 50 mL of the main culture medium having the same composition and cultured with shaking at 30° C. for 120 hours. The culture solutions were centrifuged to remove cell bodies to obtain lyophilized powders from the supernatants after removal of the cell bodies.

(3) Measurement of Nucleosidase Activity

The nucleosidase activity was defined by quantitating ribose produced by a reaction using guanosine as a substrate. In 1 mL of a reaction solution, a 0.1M acetate buffer (pH 4.3), 8 mM of guanosine and an appropriate amount of an enzyme are contained. The reaction started with addition of guanosine and was carried out at 55° C. for 30 minutes. The reaction was stopped by adding 1.5 mL of a 0.5% dinitro salicylic acid solution, and then the solution was boiled for 10 minutes. The absorbance at 540 nm of the reaction solution after cooling was measured, and the activity value was calculated from the value obtained by subtracting the absorbance of an enzyme-free reaction solution. The amount of the enzyme producing 1 μmol of ribose in 30 minutes was defined as 1 U of enzyme activity.

(4) Mashing Test

Together with 80 g of pulverized malt and 320 mL of water, each nucleosidase was added in an amount equivalent to 320 U, and a mashing test was carried out to prepare wort. The reaction process is shown in FIG. 1. The amount of each purine body in the wort after mashing was quantitatively analyzed by high performance liquid chromatography under the following conditions.

Figure 2:
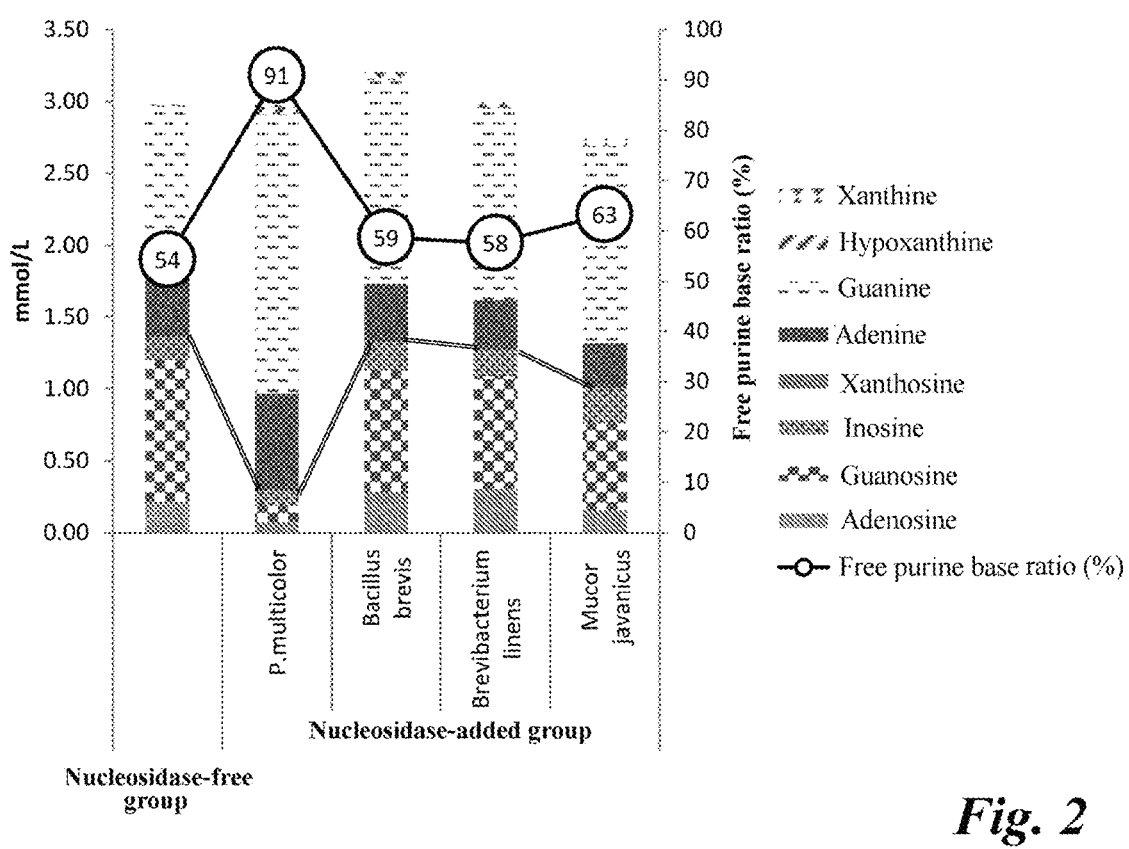
FIG. 2 Comparison in amounts of purine bodies in wort. The amounts of the respective purine bodies in the wort after mashing were analyzed by high performance liquid chromatography.

<HPLC Conditions>
Column: Asahipak GS-220 HQ
Mobile phase: 150 mM sodium phosphate buffer (pH 2.5)
Temperature: 35° C.
Flow rate: 0.5 mL/min
Detection: 260 nm The analysis results are shown in FIG. 2. In the figure, the free purine base ratio is also shown based on the following calculation formula:

Free purine base ratio (%)={purine base/(purine nucleoside+purine base)}×100.

In the wort to which the nucleosidase derived from the *Penicillium multicolor* (*P. multicolor*) IFO 7569 strain was added, the purine nucleosides decreased and the purine bases increased. In contrast, the nucleosidases from the *Bacillus brevis* IFO 15304 strain, the *Brevibacillus linens* IFO 12141 strain, and the *Mucor javanicus* 4068 strain seemed to have been probably inhibited by degradation products (adenine, guanine, hypoxanthine, and xanthine), and there were no significant changes in amounts of the purine nucleosides.

(5) Study on Properties of Nucleosidase Derived from *Penicillium multicolor* IFO 7569 Strain (*P. multicolor* Nucleosidase)

In order to investigate the properties of the *P. multicolor* nucleosidase, a solution having the following composition (hereinafter referred to as simulated wort) was used to review the operative temperature range and the operative pH range.

Figure 3:
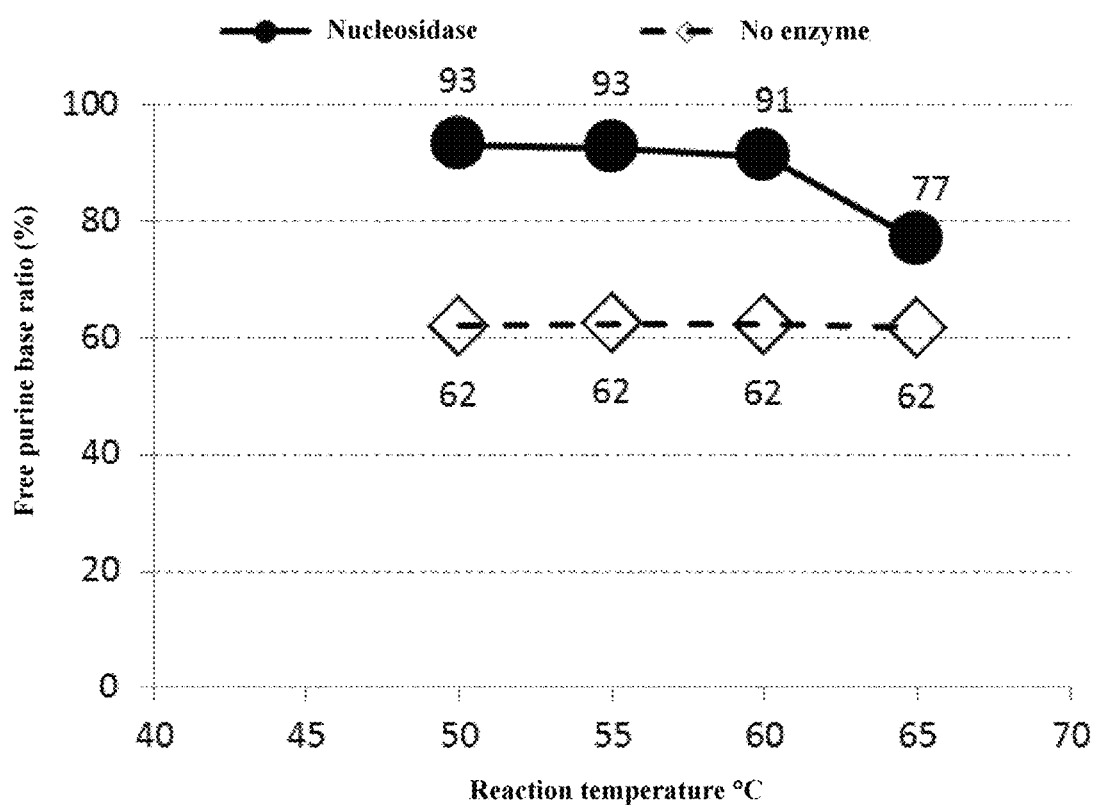
FIG. 3 Operative temperature range of a nucleosidase derived from a *Penicillium multicolor* IFO 7569 strain. An enzymatic reaction was carried out under each temperature condition in the presence of seven kinds of purine bodies, and the free purine base ratio was determined.

Adenosine 0.08 mmol/L
Adenine 0.43 mmol/L
Inosine 0.49 mmol/L
Hypoxanthine 0.08 mmol/L
Guanosine 0.67 mmol/L
Guanine 1.45 mmol/L
Xanthosine 0.00 mmol/L
Xanthine 0.08 mmol/L (5-1) Operative Temperature Range To 2 mL of simulated wort, 9 U of the *P. multicolor* nucleosidase was added to cause a reaction at pH 5.5 for 1 hour at each temperature, then diluted 10 times with a 150 mM sodium phosphate buffer (pH 2.5) as the mobile phase of HPLC, and quantitatively analyzed by high performance liquid chromatography. The free purine base ratio was calculated based on the following calculation formula. At the reaction temperature of 50° C. to 60° C., the free purine base ratio became 90% or more (FIG. 3).

Free purine base ratio (%)={purine base/(purine nucleoside+purine base)}×100.

(5-2) Operative pH Range

Figure 4:
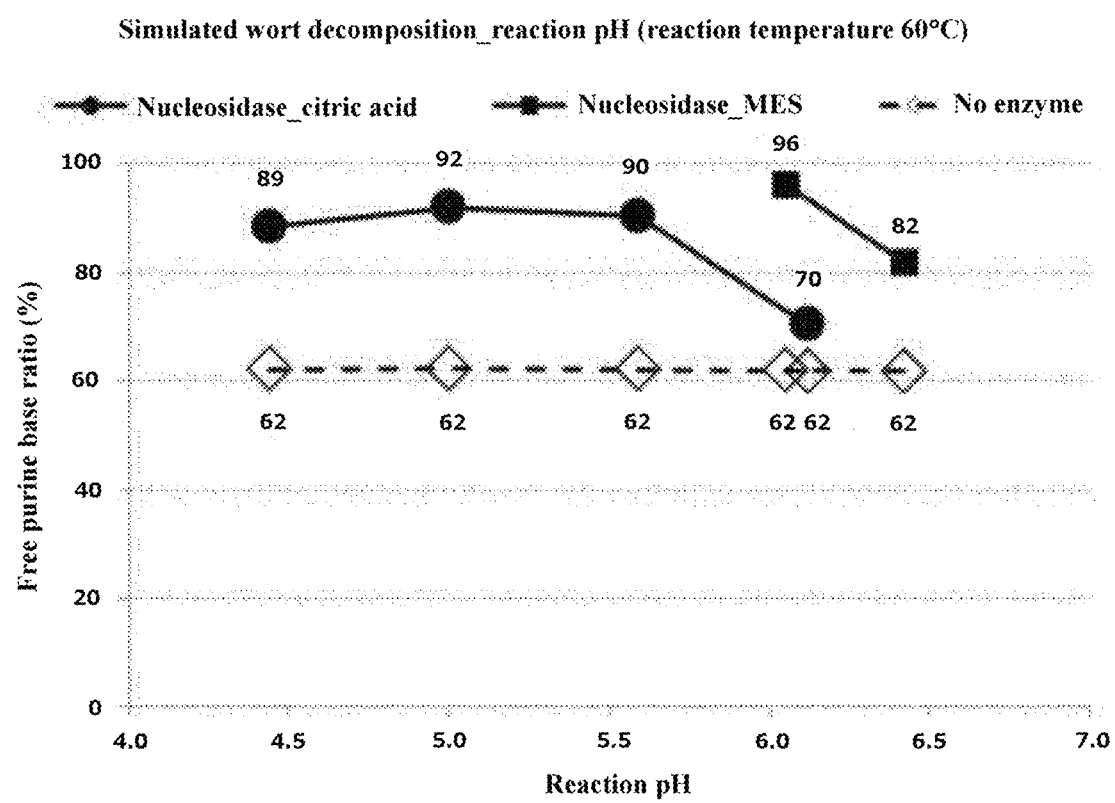
FIG. 4 Operative pH range of the nucleosidase derived from the *Penicillium multicolor* IFO 7569 strain. An enzymatic reaction was carried out under each pH condition in the presence of seven kinds of purine bodies, and the free purine base ratio was determined.

To 2 mL of simulated wort, 9 U of the *P. multicolor* nucleosidase was added to cause a reaction at 55° C. for 1 hour at each pH, then diluted 10 times with a 150 mM sodium phosphate buffer (pH 2.5) as the mobile phase of HPLC, and quantitatively analyzed by high performance liquid chromatography. A citrate buffer was used when the pH was 4.5 to 6.0, and an MES buffer was used when the pH was 6.0 to 6.5. As in the case of the study on the operative temperature range, the free purine base ratio was calculated. In the citrate buffer, the free purine body ratio was 80% or more when the pH was 4.5 to 5.5. In the MES buffer, the free purine body ratio was 80% or more when the pH was 6.0 to 6.5 (FIG. 4).

Figure 5:
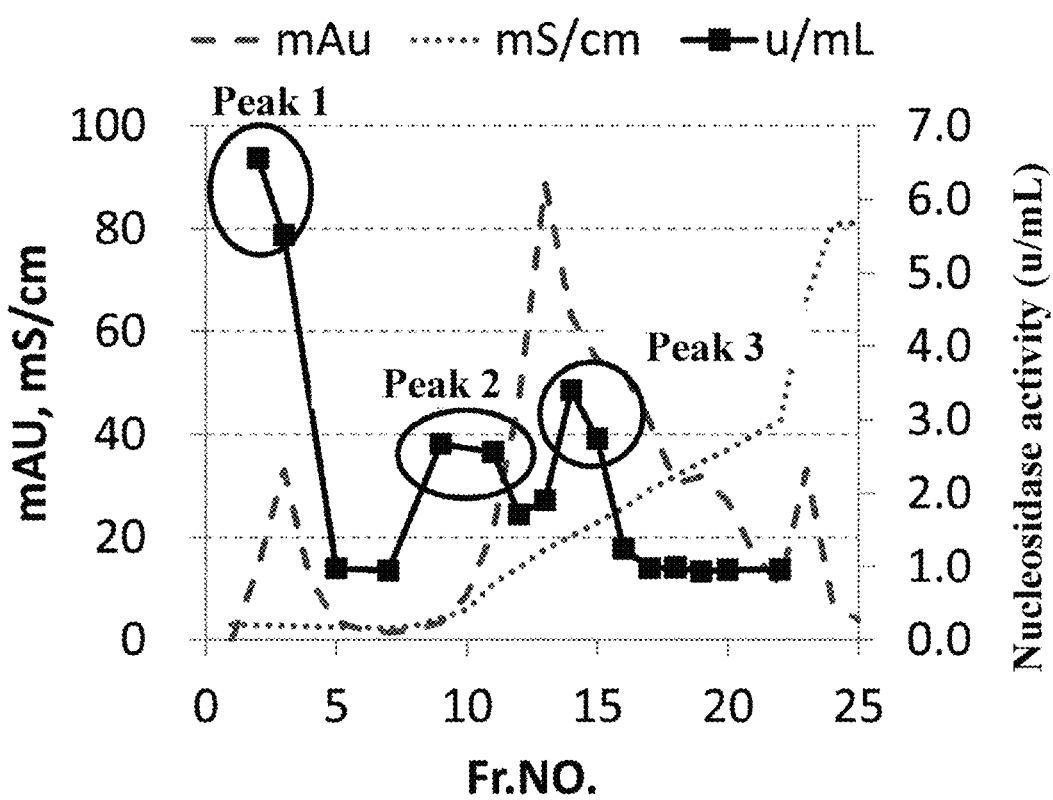
FIG. 5 Purification of the nucleosidase from the *Penicillium multicolor* IFO 7569 strain. This figure shows the results of DEAE HP column chromatography.

(6) Purification of Nucleosidase Derived from *Penicillium multicolor* IFO 7569 Strain The nucleosidase was purified by hydroxyapatite column, anion exchange column, hydrophobic column, and gel filtration column chromatographies. A series of purification processes will be shown below. First, 0.1 g of the lyophilized powder prepared from the culture solution of the *Penicillium multicolor* IFO 7569 strain was dissolved in 5 mL of a buffer (5 mM potassium phosphate buffer (pH 6)+0.3 M NaCl), and the solution was applied to a hydroxyapatite column (Bio-Rad) equilibrated with the same buffer. The adsorbed protein was eluted with a phosphoric acid gradient of 5 mM to 300 mM, and an active fraction was collected. The obtained active fraction was dialyzed against a buffer (20 mM potassium phosphate buffer (pH 5.5)) and applied to a DEAE HP column (GE Healthcare) equilibrated with the same buffer. When the adsorbed protein was eluted with an NaCl gradient of 0 mM to 500 mM, three peaks were observed (FIG. 5). Fr. 2 was defined as peak 1, Fr. 8 and Fr. 9 as peak 2, and Fr. 14 and Fr. 15 as peak 3.

Figure 6:
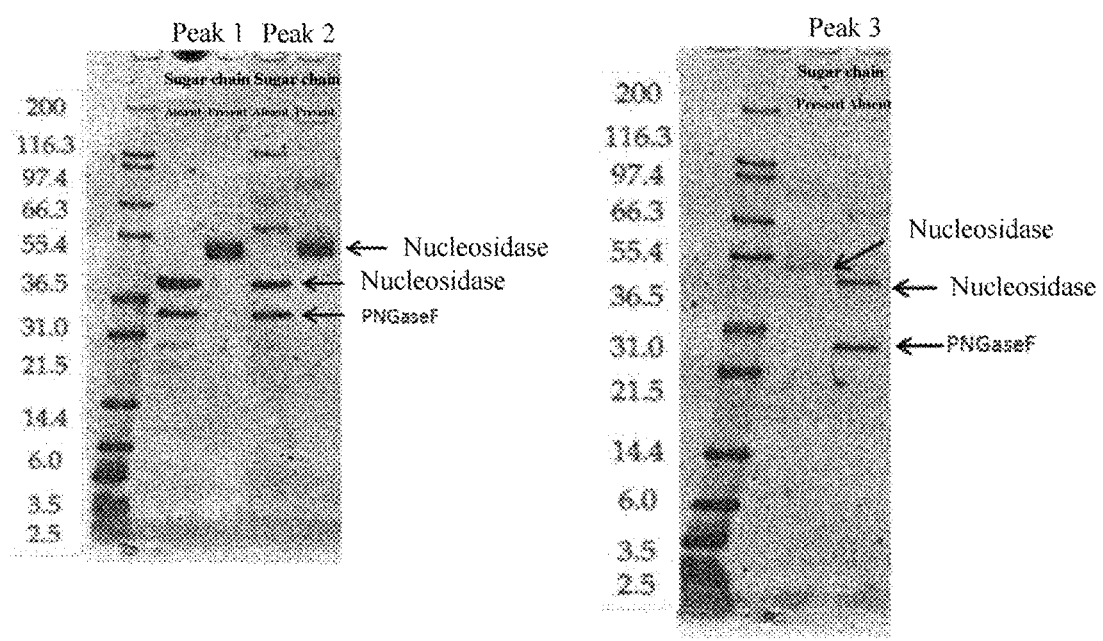
FIG. 6 Measurement results of the molecular weight of each purified enzyme (peaks 1 to 3) (SDS-PAGE). The left shows the results of peaks 1 and 2. The right shows the results of peak 3. A sample after PNGase F treatment ("sugar chain absent" lane) and an untreated sample ("sugar chain present" lane) were electrophoresed and stained with CBB. The leftmost lane shows molecular weight markers (myosin (200 kDa), β-galactosidase (116.3 kDa), phosphorylase B (97.4 kDa), BSA (66.3 kDa), glutamate dehydrogenase (55.4 kDa), lactic acid dehydrogenase (36.5 kDa), carbonate anhydrase (31.0 kDa), trypsin inhibitor (21.5 kDa), lysozyme (14.4 kDa), aprotinin (6.0 kDa), insulin B chain (3.5 kDa), and insulin A chain (2.5 kDa)).

The collected peak 3 was dialyzed against a buffer (20 mM acetate buffer (pH 4.5)+30% saturated ammonium sulfate) and applied to a Phenyl HP column (GE Healthcare) equilibrated with the same buffer. The adsorbed protein was eluted with an ammonium sulfate gradient of 30% saturation to 0%, and the active fraction was collected. The obtained active fraction was dialyzed with a buffer (20 mM sodium phosphate buffer (pH 6)) and then concentrated to 0.5 mL using an ultrafiltration membrane. The concentrated active fraction was applied to HiLoad 16/60 Superdex 200 (GE Healthcare) equilibrated with the same buffer, and an active fraction was collected. The obtained purified enzyme was confirmed to show a single band by SDS-PAGE (FIG. 6). The molecular weight was estimated to be about 53 kDa by SDS-PAGE and about 126 kDa by gel filtration chromatography (FIG. 7). The sugar chains of the resultant purified enzyme were removed with PNGase F (New England BioLabs). The treatment method was in accordance with the attached protocol. By SDS-PAGE after the treatment, it was shown that the molecular weight decreased from about 53 kDa to about 49 kDa by removal of the N-linked oligosaccharides (FIGS. 6 and 7). The collected peaks 1 and 2 were similarly purified, and their molecular weight was determined by SDS-PAGE and gel filtration chromatography. The molecular weight was estimated to be about 51 kDa by SDS-PAGE and about 230 kDa by gel filtration chromatography (FIG. 7). The sugar chains of the resultant purified enzyme were removed with PNGase F (New England BioLabs). By SDS-PAGE after the treatment, it was shown that the molecular weight decreased from about 51 kDa to about 40 kDa by removal of the N-linked oligosaccharides (FIGS. 6 and 7).

When the N-terminal amino acid sequence of the respective purified enzymes (peaks 1 to 3) were analyzed with a protein sequencer (Shimadzu Corporation), the following sequences were estimated.

N-terminal amino acid sequence of peak 1: ADKHYAIMDNDWYTA (SEQ ID NO: 7)

N-terminal amino acid sequence of peak 2: ADKHYAIMDNDWYTA (SEQ ID NO: 8)

N-terminal amino acid sequence of peak 3: VETKLIFLT (SEQ ID NO: 9)

Peak 1 and peak 2 had the same molecular weight and N-terminal amino acid sequence, and thus were estimated to be the same enzymes (FIG. 7). N-terminal amino acid sequence of peak 3 was revealed to be actually "VEILLISLT" (SEQ ID NO: 20) as a result of additional analysis. In the subsequent study, the enzyme of peak 1/peak 2 was called PN2, and the enzyme of peak 3 was called PN1.

2. Gene Cloning

The following degenerate primers were designed from the determined N-terminal amino acid sequences and nucleosidase conserved sequences, and PCR was carried out using the *P. multicolor* genomic DNA as a template.

```
<Degenerate primer for PN1>
                                   (SEQ ID NO: 10)
     FW: ACIAARTAYMGNTTYYTIAC (SEQ ID NO: 11)
     RV: CATNCCNCKNGTCCAYTGNCC <Degenerate primer for PN2>
                                   (SEQ ID NO: 12)
     FW: GCNATHATGGAYAAYGAYTGGTAYAC (SEQ ID NO: 13)
     RV: GCNGCNGTYTCRTCCCARAANGG
```

The obtained amplified fragments were subcloned into pMD20-T (TaKaRa) and sequenced. Southern blotting and colony hybridization were carried out using the probes shown in FIG. 8. The obtained fragments were sequenced to identify the base sequences (FIG. 9) in the genomes of PN1 and PN2.

Next, cDNA was prepared from mRNA prepared from the *P. multicolor* genomic DNA using SMARTER RACE 5'/3' (TaKaRa). Then, PCR was carried out using the following primers, and the amplified fragments were sequenced to determine the base sequences of PN1 and PN2 in the cDNA (FIG. 10). From the determined base sequences, amino acid sequences of PN1 and PN2 were identified (FIG. 11). In FIG. 12, PN1 and PN2 were compared.

```
<PCR primer for PN1>
                                   (SEQ ID NO: 14)
     FW: ATGGCACCTAAGAAAATCATCATTG (SEQ ID NO: 15)
     RV: TTAGTGGAAGATTCTATCGATGAGG <PCR primer for PN2>
                                   (SEQ ID NO: 16)
     FW: ATGCATTTCCCTGTTTCATTGCCGC (SEQ ID NO: 17)
     RV: TCAACGCTCATTTCTCAGGTCGG
```

3. Study on Various Properties of Enzyme PN1

(1) Optimum Temperature

Figure 13:
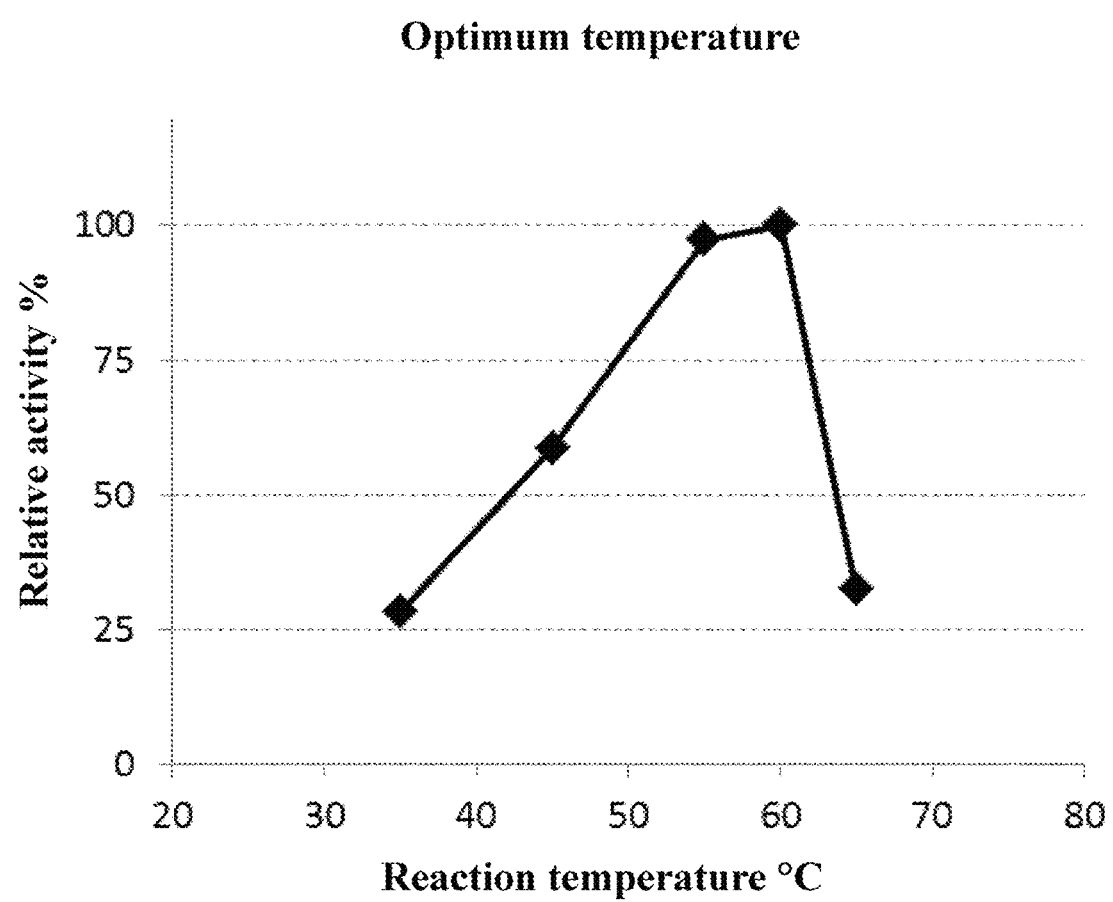
FIG. 13 Optimum temperature of the purified enzyme (PN1).

The optimum temperature of the nucleosidase (PN1) of peak 3 collected from the DEAE HP column was analyzed. The results at the respective temperatures are shown in FIG. 13. The optimum temperature under the conditions was 55° C. to 60° C.

(2) Thermal Stability

Figure 14:
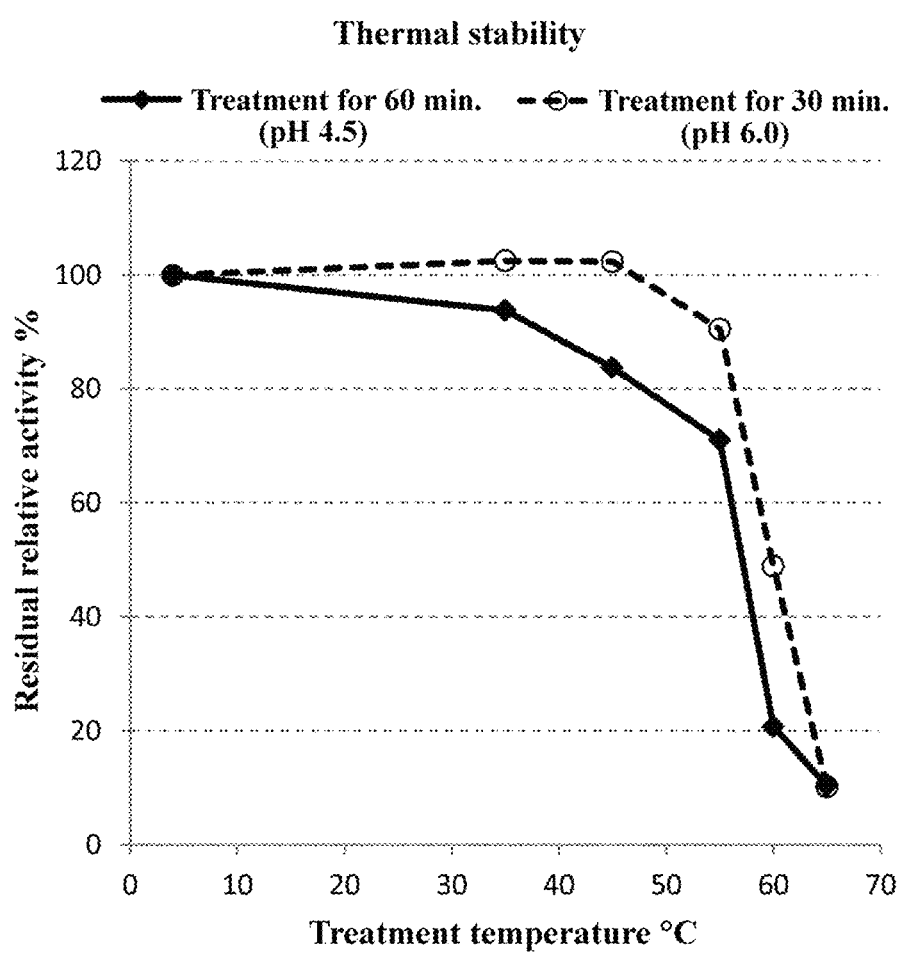
FIG. 14 Thermal stability of the purified enzyme (PN1).

The thermal stability of the nucleosidase of peak 3 collected from the DEAE HP column was analyzed. PN1 showed residual activity of 80% at up to 45° C. when treated at pH 4.5 for 60 minutes and at up to 55° C. when treated at pH 6.0 for 30 minutes (FIG. 14).

(3) Optimum pH

Figure 15:
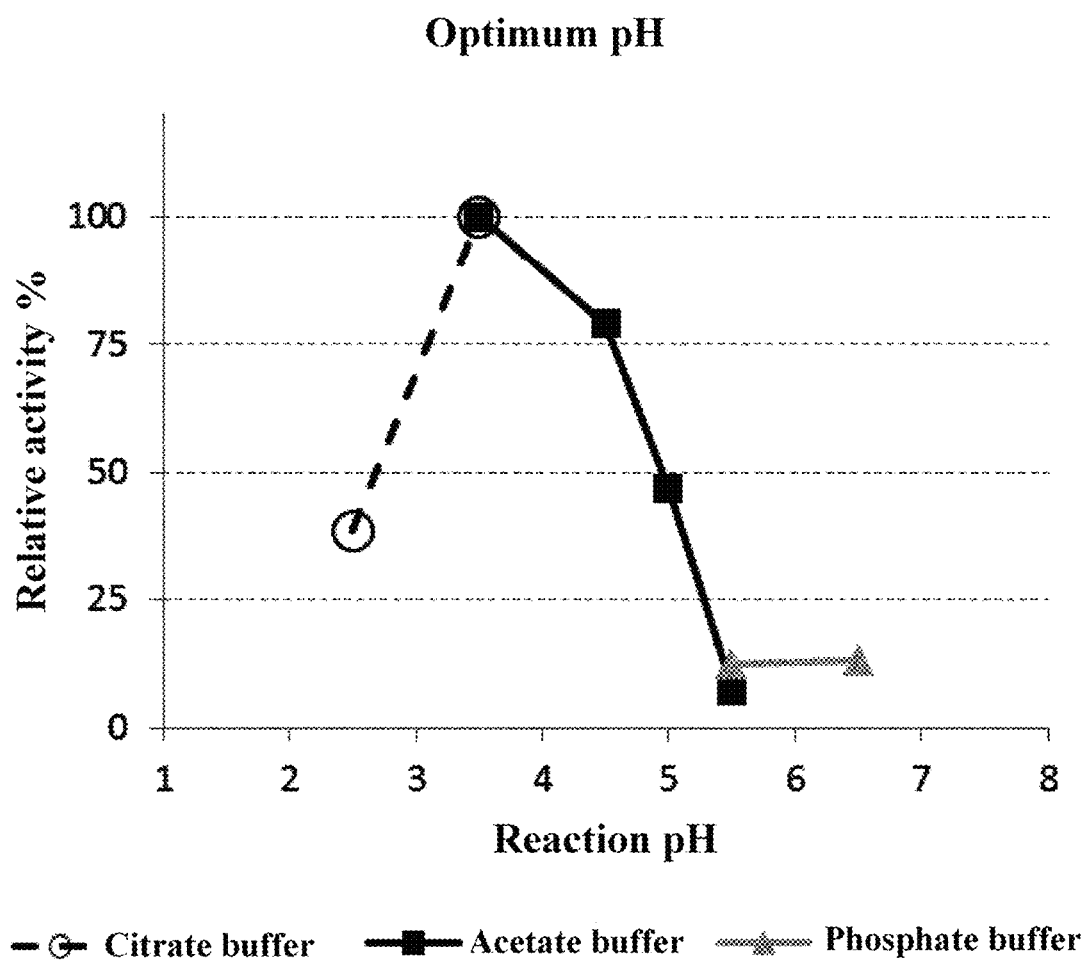
FIG. 15 Optimum pH of the purified enzyme (PN1).

The optimum pH of the nucleosidase of peak 3 collected from the DEAE HP column was analyzed. A citrate buffer was used for pH 2.5 and pH 3.5, an acetate buffer was used for pH 3.5, pH 4.5, and pH 5.5, and a potassium phosphate buffer was used for pH 5.5 and pH 6.5. The optimum pH was pH 3.5 (FIG. 15).

(4) pH Stability

Figure 16:
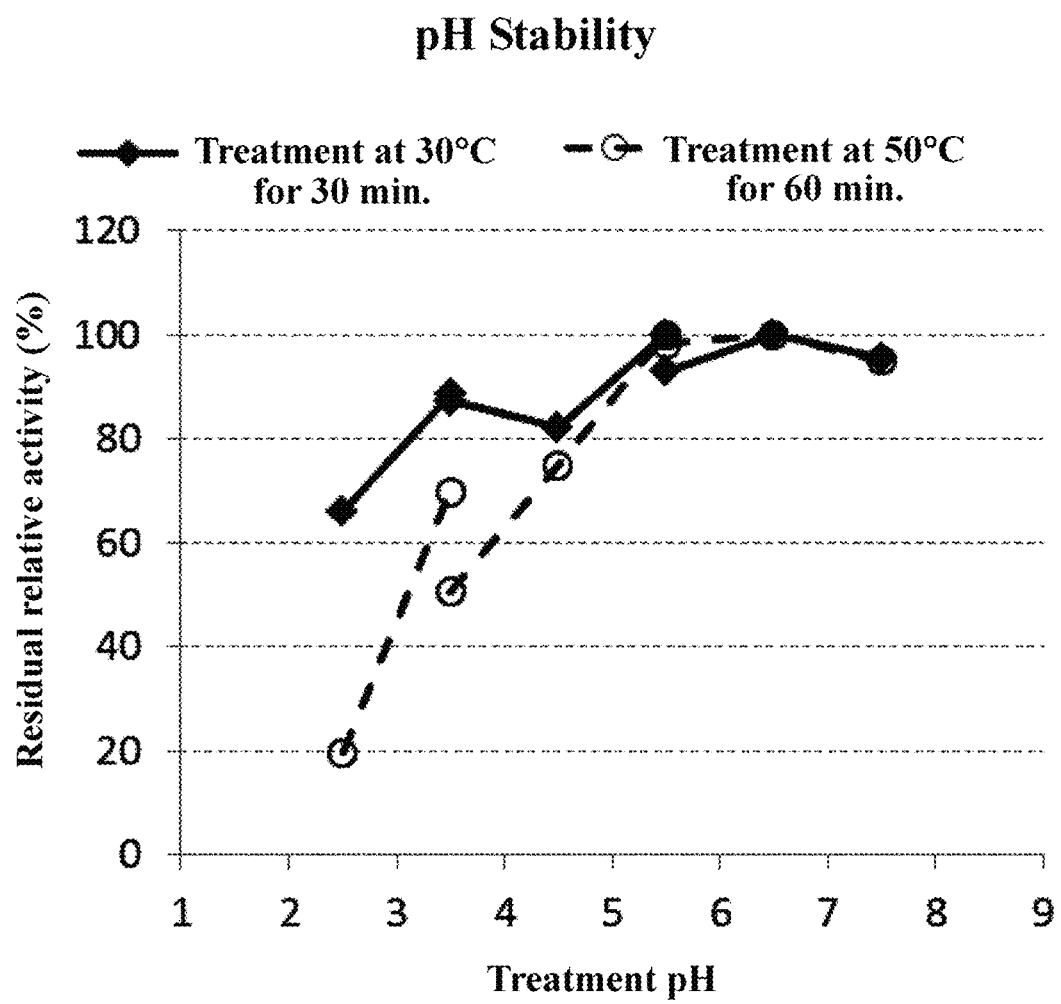
FIG. 16 pH Stability of the purified enzyme (PN1).

The pH stability of the nucleosidase of peak 3 collected from the DEAE HP column was analyzed when treatment was carried out at 30° C. for 30 minutes and at 50° C. for 60 minutes, respectively, at each pH. The same buffers were used as those used for the study on the optimum pH, and a potassium phosphate buffer was used for pH 7.5. The nucleosidase showed residual activity of 80% or more at a pH of 3.5 to 7.5 when treated at 30° C. for 30 minutes and at a pH of 3.5 to 7.5 when treated at 50° C. for 60 minutes (FIG. 16).

4. Recombinant Production of Enzyme PN2

Figure 17:
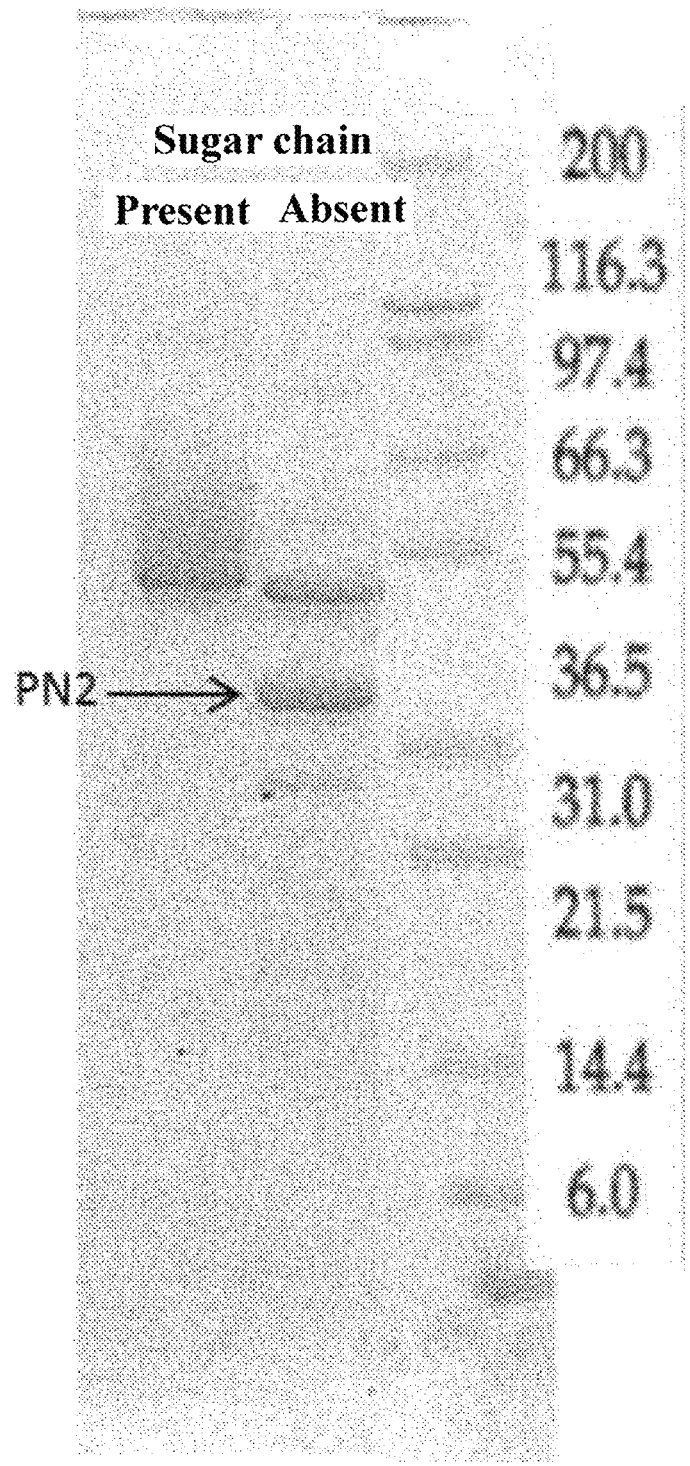
FIG. 17 Results of electrophoresis of the recombinantly produced enzyme (PN2).

The cDNA fragment of PN2 was inserted into the cloning site of an expression vector to construct a PN2 expression vector. The expression vector was used to transform *Aspergillus oryzae* (*A. oryzae* (pyrG-)). The obtained transformant was cultured in liquid for 4 days (30° C., 300 rpm). The culture supernatant was collected to measure the nucleosidase activity. As a result, it was revealed that a transformant showing activity was obtained. In addition, when the culture supernatant was subjected to sugar chain removal treatment and electrophoresis, a band having a size consistent with the estimated molecular weight was confirmed (FIG. 17).

5. Study on Various Properties of Enzyme PN2

Recombinantly produced PN2 was used to study various properties. Experiment methods, conditions, and the like were the same as in the case of the study on PN1.

(1) Optimum Temperature

Figure 18:
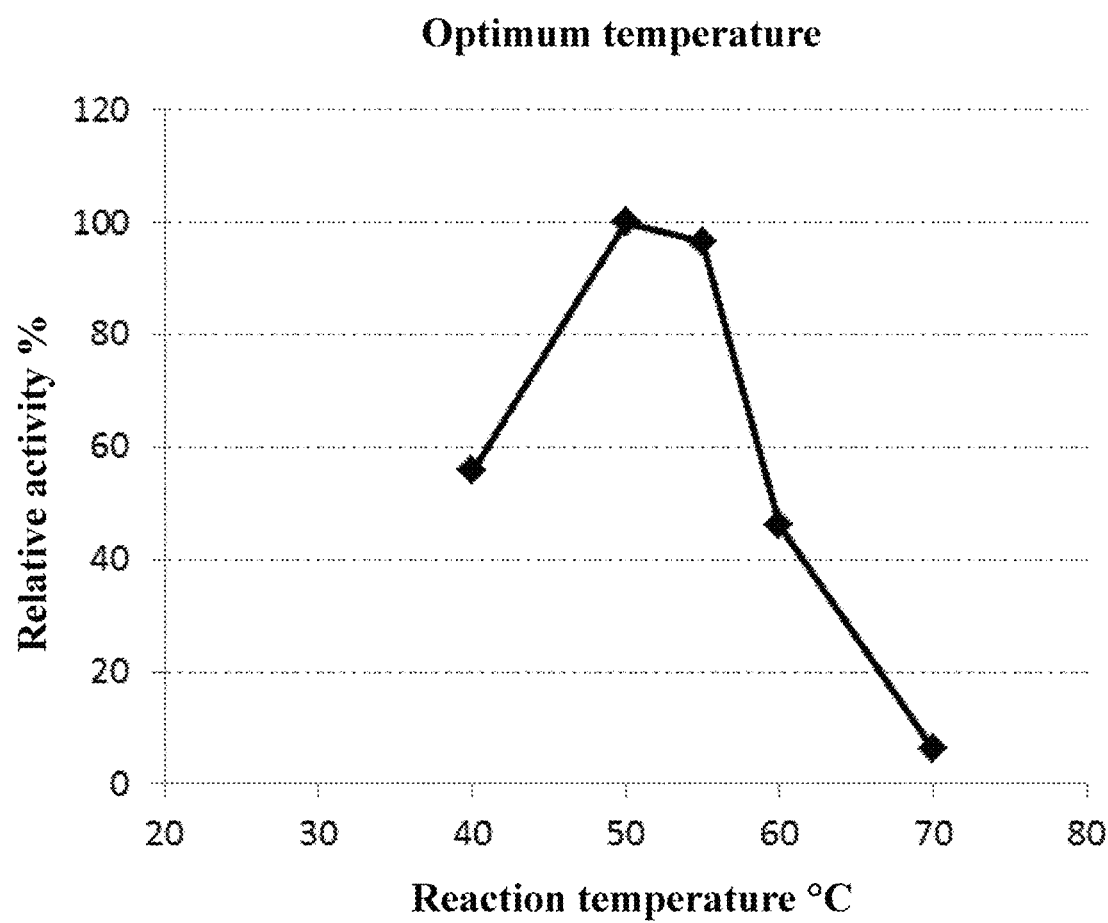
FIG. 18 Optimum temperature of the purified enzyme (PN2).

The optimum temperature was 50° C. to 55° C. (FIG. 18).

(2) Thermal Stability

Figure 19:
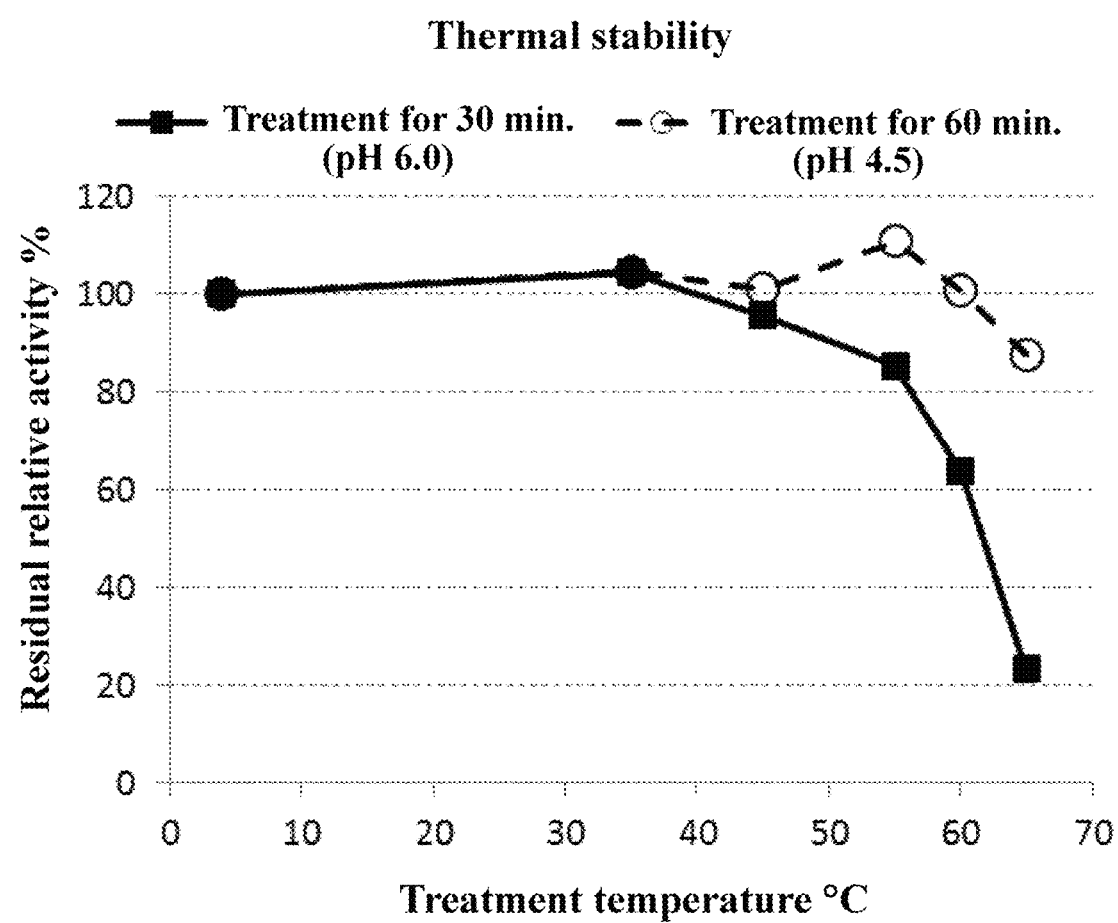
FIG. 19 Thermal stability of the purified enzyme (PN2).

PN2 showed residual activity of 80% at up to 65° C. when treated at pH 4.5 for 60 minutes and at up to 55° C. when treated at pH 6.0 for 30 minutes (FIG. 19).

(3) Optimum pH

Figure 20:
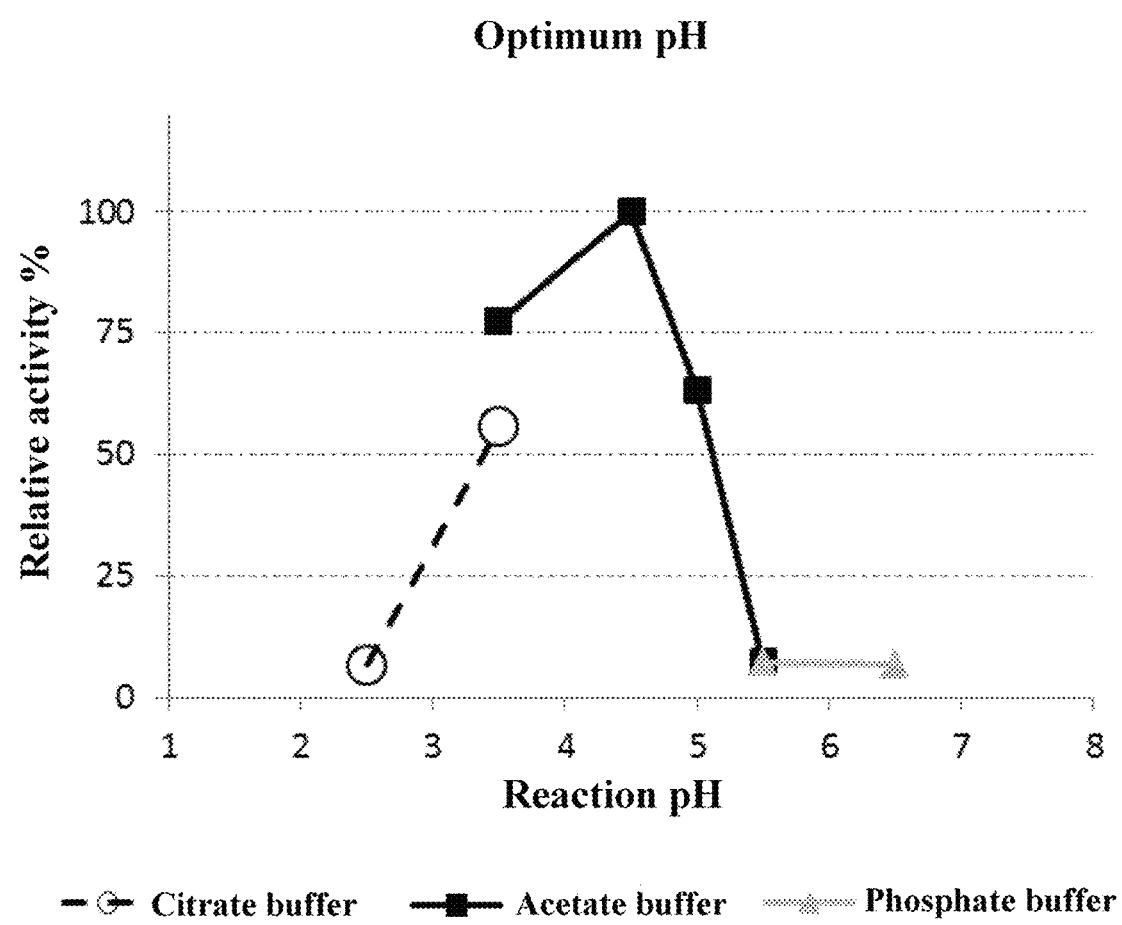
FIG. 20 Optimum pH of the purified enzyme (PN2).

A citrate buffer was used for pH 2.5 and pH 3.5, an acetate buffer was used for pH 3.5, pH 4.5, and pH 5.5, and a potassium phosphate buffer was used for pH 5.5 and pH 6.5. The optimum pH was 4.5 (FIG. 20).

(4) pH Stability

Figure 21:
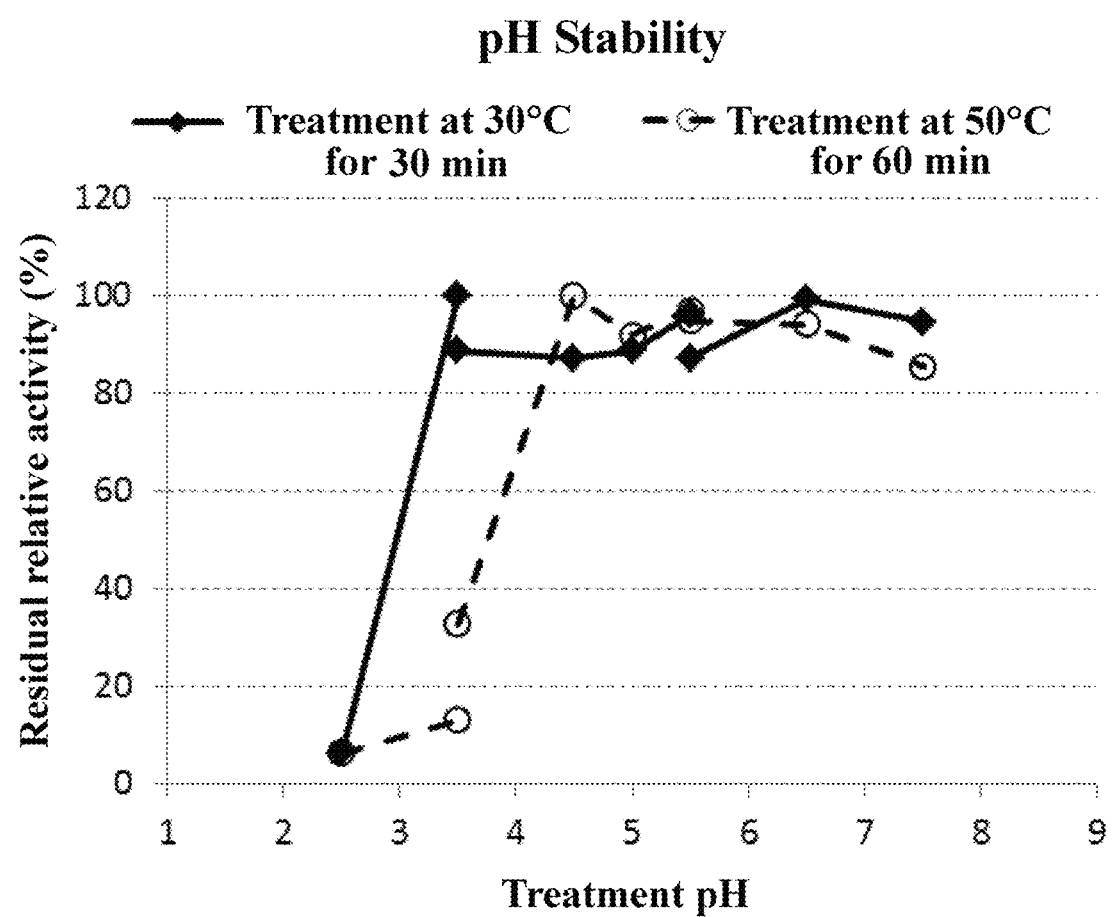
FIG. 21 pH Stability of the purified enzyme (PN2).

The pH stability was analyzed when treatment was carried out at 30° C. for 30 minutes and at 50° C. for 60 minutes, respectively, at each pH. The same buffers were used as those used for the study on the optimum pH. PN2 showed residual activity of 80% or more at a pH of 3.5 to 7.5 when treated at 30° C. for 30 minutes and a pH of 4.5 to 7.5 when treated at 50° C. for 60 minutes (FIG. 21).

6. Mashing Test on Enzyme PN2

Figure 22:
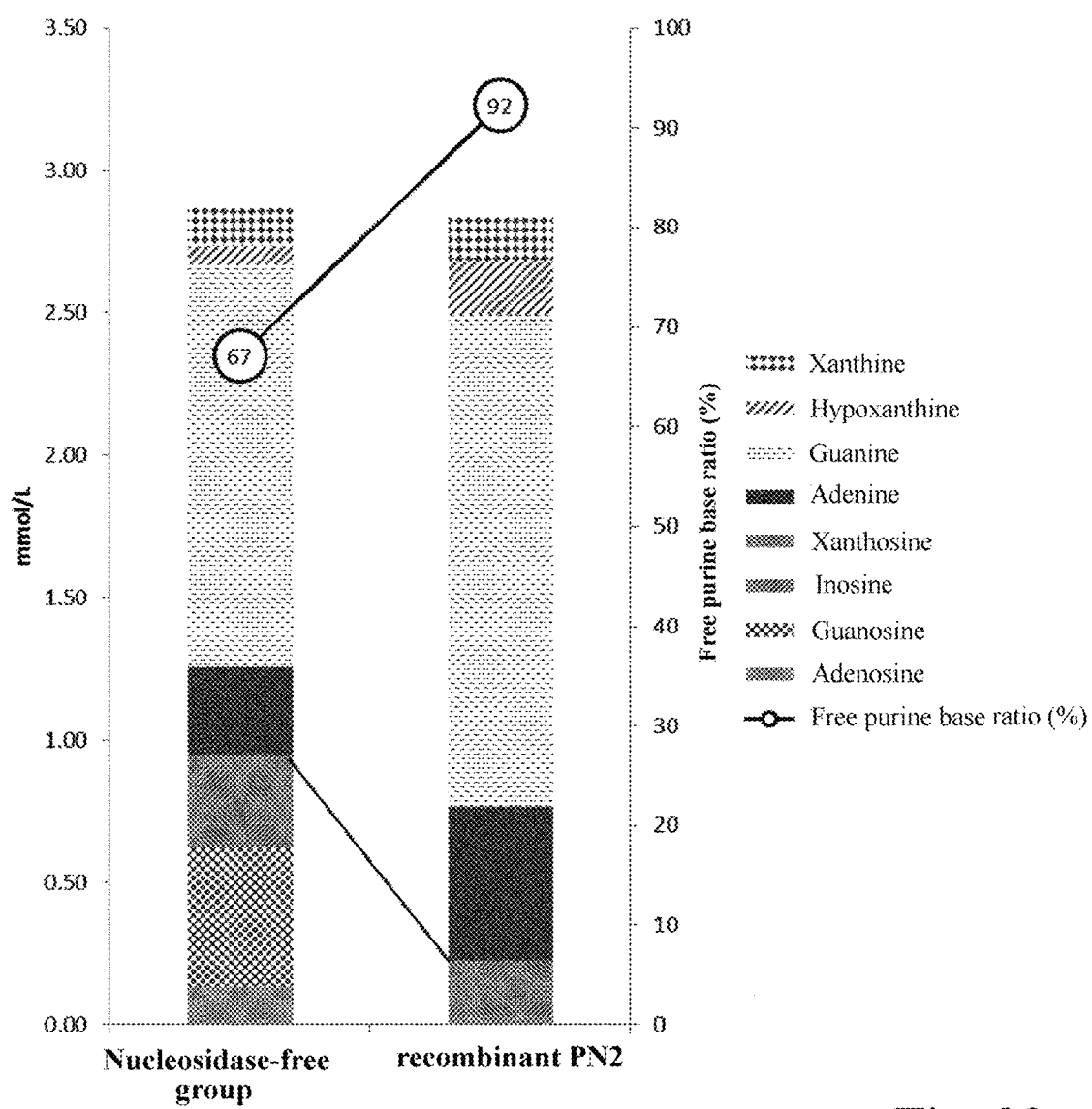
FIG. 22 Results of a mashing (preparation) test using the recombinantly produced enzyme (PN2).

A mashing test was conducted using recombinantly produced PN2. Test methods, conditions, and the like were the same as in the above 1. (4). The amount of each purine body in the wort after mashing was quantitatively analyzed by high performance liquid chromatography. The analysis results are shown in FIG. 22. It can be seen that, in the wort to which PN2 (nucleosidase) was added, the purine nucleosides decrease and the purine bases increase.

7. Mashing Test Under Low-pH Conditions

Figure 23:
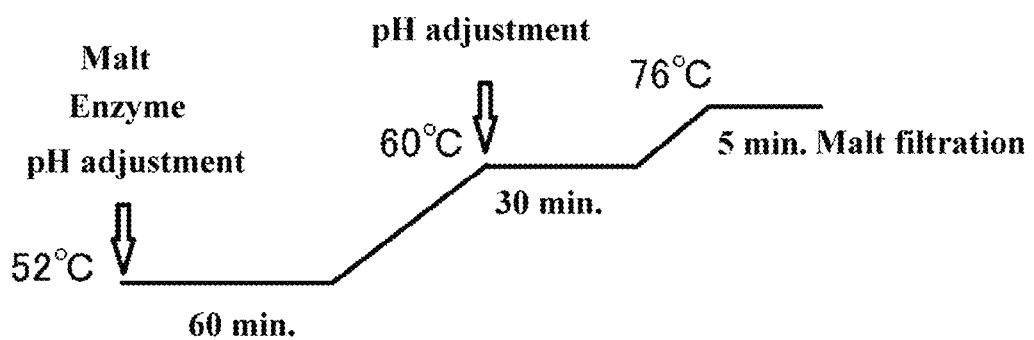
FIG. 23 Reaction process of the mashing (preparation) test.
Figure 24:
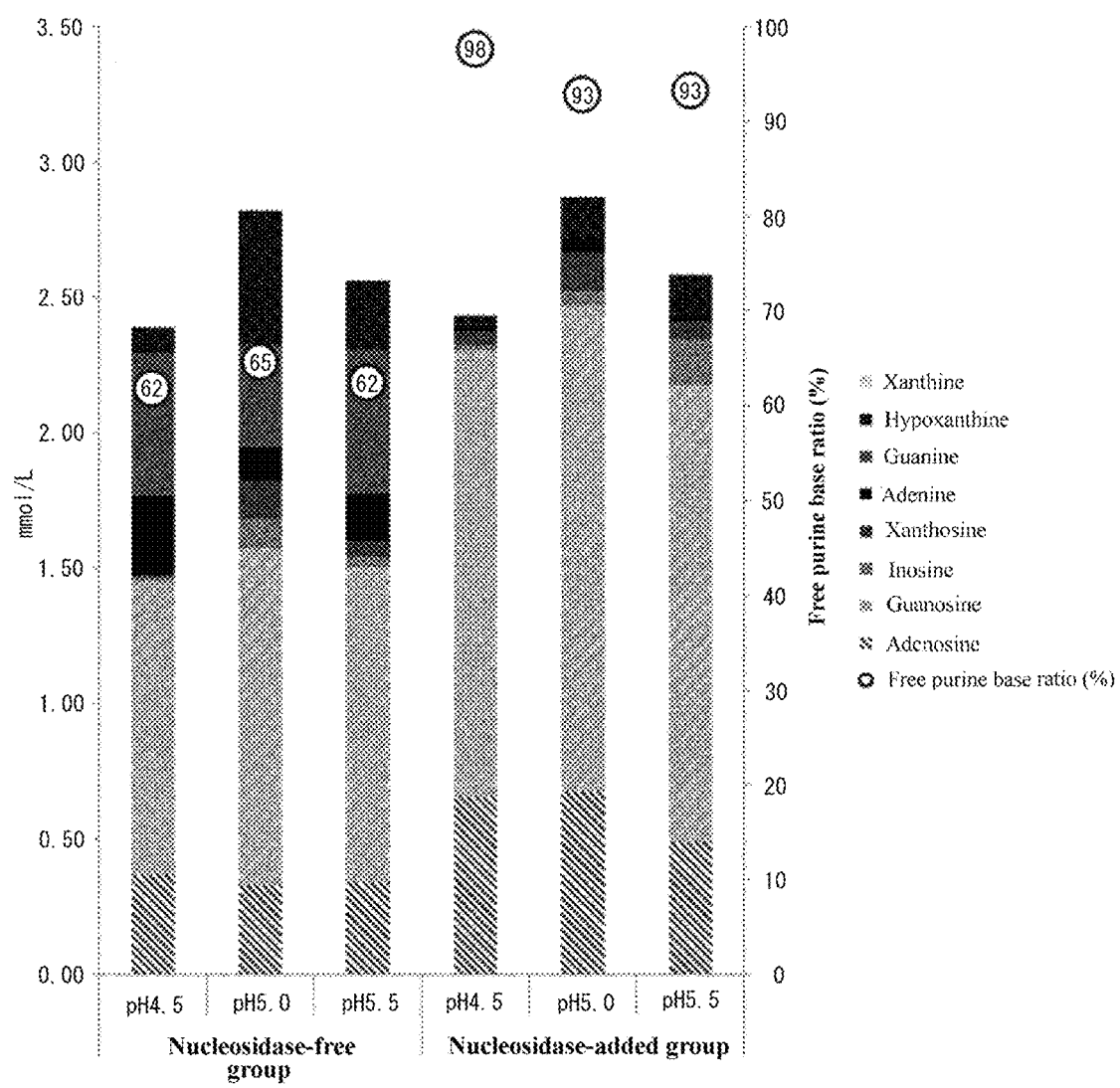
FIG. 24 Comparison in amounts of purine bodies in wort. The mashing test was carried out at a pH of 4.5 to 5.5. The amounts of the respective purine bodies in the wort after mashing were analyzed by high performance liquid chromatography.

In order to further confirm the usefulness of the nucleosidase derived from the *Penicillium multicolor* IFO 7569 strain in the production of beer or beer-based beverages, a mashing test was carried out at a pH around the optimum pH (pH 4.5 to 5.5) of the enzyme to study whether the desired effect (that is, reduction in purine bodies) could be obtained. Together with 80 g of pulverized malt and 320 mL of water, the nucleosidase was added in an amount equivalent to 2400 U, and the pH at the initial (52° C.) and 60° C. processes were each adjusted to pH 4.5, pH 5.0, or pH 5.5, and a mashing test was conducted to prepare wort. The reaction process is shown in FIG. 23. The amount of each purine body in the wort after mashing was quantitatively analyzed by high performance liquid chromatography under the following conditions. The analysis results are shown in FIG. 24. Even when mashing was carried out at a pH of 4.5 to 5.5, this nucleosidase had a free purine base ratio of 90% or more, and it can be seen that the purine nucleosides sufficiently decrease and the purine bases increase. (FIG. 24)

<HPLC Conditions>

Column: Asahipak GS-220 HQ

Mobile phase: 150 mM sodium phosphate buffer (pH 2.5)

Temperature: 35° C.

Flow rate: 0.5 mL/min

Detection: 260 nm

8. Conclusion

The nucleosidase derived from the *Penicillium multicolor* IFO 7569 strain showed an optimum temperature and thermal stability suitable for use in the beer preparation process. It was also found that the nucleosidase is excellent in pH stability and thermal stability, and can be applied not only to the production of beer or beer-based beverages but also to various uses. In this way, the inventors have succeeded in obtaining a novel nucleosidase extremely useful for reducing purine bodies in beverages and foods.

Example 2 Preparation of Nucleosidase Preparation

A mutant strain of the *Penicillium multicolor* IFO 7569 strain was inoculated into 100 mL of the following culture medium B and cultured with shaking in a Sakaguchi flask with a volume of 500 mL at 27° C. for 48 to 72 hours. This preculture solution was transferred to 2 L of the following culture medium B and cultured with aeration and agitation at 27° C. for 190 to 240 hours. This culture solution was filtered through diatomaceous earth to remove cell bodies. The culture supernatant obtained after removal of the cell bodies was concentrated with an ultrafiltration membrane to obtain a nucleosidase enzyme solution. Nucleosidase enzyme solutions (Samples 1 to 3) were prepared using three kinds of mutant strains different in guanine deaminase-producing ability.

<Culture Medium A>

1% Lustergen FK (Nippon Starch Chemical Co., Ltd.)

1% Yeast extract (Difco)

0.5% NaCl pH 7.0

<Culture Medium B>

1% Lustergen FK (Nippon Starch Chemical Co., Ltd.)

1% Yeast extract (Difco)

2% Cornmeal (Matsumoto Nosan K.K.)

0.5% NaCl pH 6.5

Example 3 Xanthine Production Test

To 0.8 ml of a 150 mM sodium acetate buffer (pH 4.3), 0.1 ml of a 1 mM guanine solution dissolved in 50 mM hydrochloric acid was added to prepare a substrate solution. To 0.9 ml of the substrate solution, 0.1 ml of each of the nucleosidase enzyme solutions (Samples 1 to 3) diluted with purified water so that the nucleosidase activity would be 500 u/g was added to cause a reaction at 52° C. After 1 hour, 0.1 ml of each of the reaction solutions was sampled. The enzymatic reaction was stopped by 10-minute boiling, and then the solution was diluted twice with purified water and caused to pass through a 0.45-μm membrane filter. The solution after filter treatment was subjected to HPLC to quantify the amount of xanthine produced.

(HPLC Analysis Conditions)
Column: Asahipak GS220-HQ No. M211036
Solvent: 150 mM sodium dihydrogen phosphate, pH 2.5
Flow rate: 0.5 ml/min
Column temperature: 35° C.
Injection volume: 10 μL
Detection: 260 nm
Analysis time: 60 minutes The amount of enzyme converting 1 pmol of guanine into xanthine per minute was defined as 1 U, and the guanine deaminase activity of each of the nucleosidase enzyme solutions was calculated based on the following calculation formula.

$$\text{Guanine deaminase activity (u/ml)} = \text{amount of xanthine produced in 60 minutes of reaction (μmol/ml)} \times 1/60 \times 1000000$$

On the other hand, by the method described in "(3) Measurement of nucleosidase activity" in Example 1, the nucleosidase activity of each of the nucleosidase enzyme solutions (Samples 1 to 3) was determined to calculate the guanine deaminase activity (u/u) per nucleosidase activity (Table 1).

TABLE 1

Comparison in guanine deaminase activity

|  | Amount of xanthine produced (μmol/ml) | Guanine deaminase activity (u/ml) | Guanine deaminase activity per nucleosidase activity (u/u) |
|---|---|---|---|
| Sample 1 | 0.003 | 43 | 0.086 |
| Sample 2 | 0.018 | 300 | 0.6 |
| Sample 3 | 0.000 | 0 | 0 |

Example 4 Mashing Test

A mashing test was conducted using the nucleosidase enzyme solutions (Samples 1 to 3) of Example 2 to investigate the assimilable purine constituent ratio. Together with 80 g of pulverized malt and 320 mL of water, the nucleosidase was added in an amount equivalent to 2400 U, and the pHs at the initial (52° C.) and 60° C. processes were each adjusted to pH 4.5, and a mashing test was conducted to prepare wort. The reaction process is shown in FIG. 23. The amount of each purine body in the wort after mashing was quantitatively analyzed by high performance liquid chromatography under the following conditions.

<HPLC Conditions>
Column: Asahipak GS-220 HQ
Mobile phase: 150 mM sodium phosphate buffer (pH 2.5)
Temperature: 35° C.
Flow rate: 0.5 mL/min
Detection: 260 nm The assimilable purine constituent ratios of the respective nucleosidase enzyme solutions were calculated based on the following calculation formula and compared with each other (Table 2). The assimilable purine constituent ratio is a ratio of assimilable purines (adenine and guanine) to non-assimilable purines (adenosine, guanosine, inosine, xanthosine, xanthine, and hypoxanthine).

$$\text{Assimilable purine constituent ratio (\%)} = \text{assimilable purine amount}/(\text{assimilable purine amount} + \text{non-assimilable purine amount}) \times 100$$

TABLE 2

|  | Guanine deaminase activity (u/ml) | Guanine deaminase activity per nucleosidase activity (u/u) | Assimilable purine constituent ratio (%) |
|---|---|---|---|
| Sample 1 | 43 | 0.086 | 95 |
| Sample 2 | 300 | 0.6 | 87 |
| Sample 3 | 0 | 0 | 95 |
| No enzyme | — | — | 49 |

From the above experimental results, the relationship between the guanine deaminase activity per nucleosidase activity and the assimilable purine constituent ratio is as shown in FIG. 25. Therefore, in order to attain an assimilable purine constituent ratio of 90% or more, the guanine deaminase activity per nucleosidase activity is 0.4 (U/U) or less, and it could be confirmed that the nucleosidase enzyme solution satisfying this condition (Sample 1) was obtained.

INDUSTRIAL APPLICABILITY

The nucleosidase preparation of the present invention has a low contaminant guanine deaminase activity and is useful for producing low-purine beer/beer-based beverages. The present invention can be used for producing various low-purine foods or beverages as well as low-purine beer/beer-based beverages.

The present invention is not limited to the above description of the embodiments and examples of the present invention at all. Various modifications that can be easily achieved by those skilled in the art without departing from the claims also fall within the scope of the present invention. The contents of the articles, patent laid-open publications, patent publications, and the like specified herein shall be cited by incorporation in their entity.

[Sequence Listing]

The invention claimed is:

1. A manufactured nucleosidase preparation having an activity ratio (U/U), which is guanine deaminase activity per nucleosidase activity, of 0.4 or less;
wherein the manufactured nucleosidase preparation contains a nucleosidase having an amino acid sequence having 92% or more identity with the amino acid sequence of SEQ ID NO: 22 and at least one manufactured agent selected from a group comprising of an excipient, a buffer agent, a suspending agent, a stabilizer, a preservative, an antiseptic, and a saline;
and the nucleosidase has been collected from a culture producing said nucleosidase.

2. The nucleosidase preparation according to claim 1, wherein the activity ratio is 0.36 or less.

3. The nucleosidase preparation according to claim 1, wherein the amino acid sequence of the nucleosidase is an amino acid sequence having 95% or more identity with the amino acid sequence of SEQ ID NO: 22.

4. The nucleosidase preparation according to claim 1, wherein the contained nucleosidase has the following enzymological properties:
(1) action: catalyzing a reaction of hydrolyzing purine nucleosides into D-ribose and purine bases and exhibiting activity even in the presence of adenosine, adenine, inosine, hypoxanthine, guanosine, guanine, and xanthine;
(2) optimum temperature: 55° C. to 60° C.; and
(3) thermal stability: stable at 55° C. or lower (pH 6.0, for 30 minutes).

5. The nucleosidase preparation according to claim 4, wherein the contained nucleosidase further has the following enzymological properties:
(4) optimum pH: 3.5; and
(5) pH stability: stable in the range of pH 3.5 to 7.5 (30° C., 30 minutes).

6. The nucleosidase preparation according to claim 1, wherein nucleosidase contained in the preparation has the following enzymological properties:
(1) action: catalyzing a reaction of hydrolyzing purine nucleosides into D-ribose and purine bases and exhibiting activity even in the presence of adenosine, adenine, inosine, hypoxanthine, guanosine, guanine, and xanthine;
(2) optimum temperature: 50° C. to 55° C.; and
(3) thermal stability: stable at 65° C. or lower (pH 4.5, for 60 minutes).

7. The nucleosidase preparation according to claim 6, wherein the contained nucleosidase further has the following enzymological properties:
(4) optimum pH: 4.5; and
(5) pH stability: stable in the range of pH 3.5 to 7.5 (30° C., 30 minutes).

8. The nucleosidase preparation according to claim 1, wherein the nucleosidase is derived from *Penicillium* multicolor.

9. The nucleosidase preparation according to claim 8, wherein the *Penicillium* multicolor is an IFO 7569 strain or a mutant strain thereof.

10. A manufactured nucleosidase preparation having an activity ratio (U/U), which is guanine deaminase activity per nucleosidase activity, of 0.4 or less;
wherein the manufactured nucleosidase preparation contains a nucleosidase having an amino acid sequence having 92% or more identity with the amino acid sequence of SEQ ID NO: 22 and contains at least one substitution modification relative to SEQ ID NO: 22;
and the nucleosidase has been collected from a culture producing said nucleosidase.

* * * * *